US006366814B1

(12) United States Patent
Boveja et al.

(10) Patent No.: US 6,366,814 B1
(45) Date of Patent: Apr. 2, 2002

(54) EXTERNAL STIMULATOR FOR ADJUNCT (ADD-ON) TREATMENT FOR NEUROLOGICAL, NEUROPSYCHIATRIC, AND UROLOGICAL DISORDERS

(76) Inventors: Birinder R. Boveja, 8879 S. Chestnut Hill Way; Alok Sarwal, 9709 S. Townville Cir., both of Highlands Ranch, CO (US) 80130

( * ) Notice: Subject to any disclaimer, the term of this patent is extended or adjusted under 35 U.S.C. 154(b) by 0 days.

(21) Appl. No.: 09/751,966

(22) Filed: Dec. 29, 2000

Related U.S. Application Data

(63) Continuation-in-part of application No. 09/178,060, filed on Oct. 26, 1998, now Pat. No. 6,205,359.

(51) Int. Cl.[7] ................................................ A61N 1/36
(52) U.S. Cl. ...................................................... 607/45
(58) Field of Search ............................. 607/40, 41, 45, 607/46, 59, 61, 66

(56) References Cited

U.S. PATENT DOCUMENTS

| 3,796,221 A | | 3/1974 | Hagfors et al. .............. 128/421 |
| 3,918,461 A | * | 11/1975 | Cooper ........................ 607/45 |
| 4,622,973 A | * | 11/1986 | Agarwala .................... 607/59 |
| 4,702,254 A | | 10/1987 | Zabara et al. ............... 128/421 |
| 4,771,779 A | | 9/1988 | Tanagho et al. ........ 128/419 E |
| 4,867,164 A | | 9/1989 | Zabara et al. ................ 128/421 |
| 5,025,807 A | | 6/1991 | Zabara et al. ................ 128/421 |
| 5,299,569 A | | 4/1994 | Zabara et al. .................. 607/45 |
| 5,304,206 A | | 4/1994 | Baker et al. .................... 607/2 |
| 5,540,734 A | | 7/1996 | Zabara et al. ................. 607/46 |

OTHER PUBLICATIONS

McLachlan, R.S., Feb. 1998, "Vagus nerve stimulation for treatment of seizures" Arch Neural/vol. 55, 232–233, P–233 Used.

* cited by examiner

*Primary Examiner*—William E. Kamm

(57) ABSTRACT

An external stimulator adapted to be inductively coupled with an implanted lead-receiver is designed to deliver neuromodulation therapy for disorders including depression, migraine, partial complex epilepsy, generalized epilepsy, involuntary movement disorders, dementia, obsessive compulsive disorders, urinary incontinence, neurogenic/psychogenic pain and bladder control. The external stimulator containing limited number of predetermined programs packaged into the stimulator, giving the patient or caretaker a way to adjust the therapy within confined limits, or turn the device off. The pre-packaged programs contain unique combination of pulse amplitude, pulse width, frequency of stimulation, and on-off time. The programs are capable of being modified with a programming station connected to the pulse generator with a RS232-C serial connection.

45 Claims, 26 Drawing Sheets

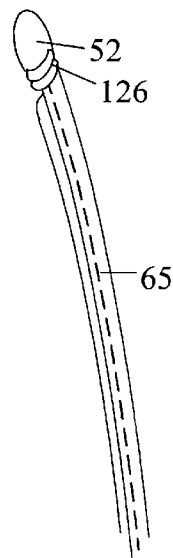
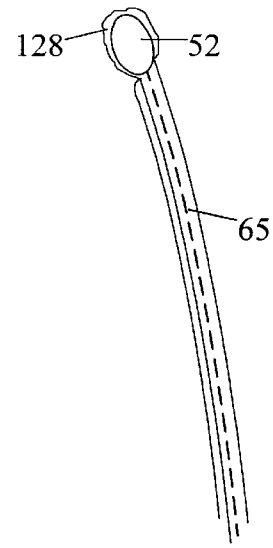
FIG. 21  FIG. 22
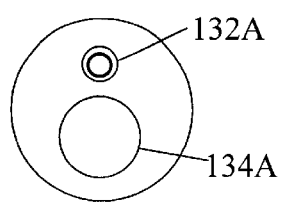
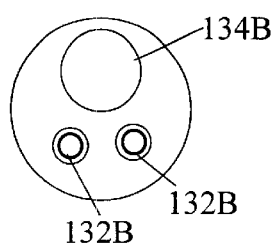
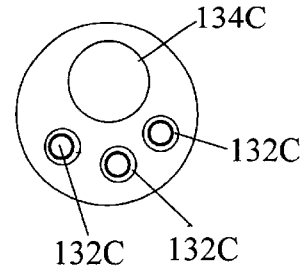
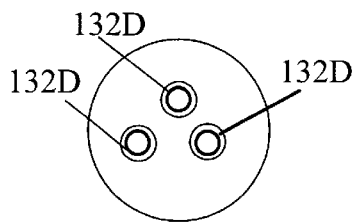
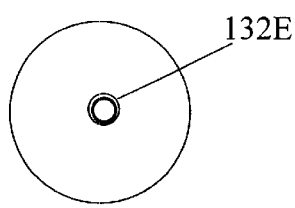
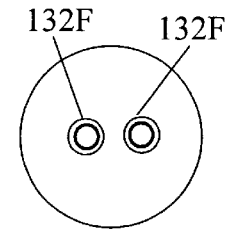
FIG. 23

EXTERNAL STIMULATOR FOR ADJUNCT (ADD-ON) TREATMENT FOR NEUROLOGICAL, NEUROPSYCHIATRIC, AND UROLOGICAL DISORDERS

This is a Continuation-in-Part application claiming priority from prior application Ser. No. 09/178,060 filed Oct. 26, 1998, now U.S. Pat. No. 6,205,359 the prior application being incorporated herein by reference. Further, it is related to application Ser. No. 09/752,083 filed Dec. 29, 2000 entitled ELECTRICAL STIMULATION ADJUNCT (ADD-ON) THERAPY FOR URINARY INCONTINENCE, AND UROLOGICAL DISORDERS USING AN EXTERNAL STIMULATOR.

FIELD OF INVENTION

This invention relates generally to electrical stimulation therapy for medical disorders, more specifically to neuromodulation therapy for neurological, neuropsychiatric, and urological disorders with an external stimulator containing predetermined programs, and adapted to be used with an implanted lead-receiver.

BACKGROUND

Medical research has shown beneficial medical effects of vagus nerve stimulation (VNS) for severely depressed patients and for other neurological disorders. Vagus nerve stimulation, and the profound effects of electrical stimulation of the vagus nerve on central nervous system (CNS) activity, extends back to the 1930's. Medical studies in clinical neurobiology have advanced our understanding of anatomic and physiologic basis of the anti-depressive effects of vagus nerve stimulation.

Some of the somatic interventions for the treatment of depression include electroconvulsive therapy (ECT), transcranial magnetic stimulation, vagus nerve stimulation, and deep brain stimulation. The vagus nerve is the 10 th cranial nerve, and is a direct extension of the brain. FIG. 1A, shows a diagram of the brain and spinal cord 24, with its relationship to the vagus nerve 54 and the nucleus tractus solitarius 14. FIG. 1B shows the relationship of the vagus nerve 54 with the other cranial nerves.

Vagus nerve stimulation is a means of directly affecting central function and is less invasive than deep brain stimulation (DBS). As shown in FIG. 1C, cranial nerves have both afferent pathway 19 (inward conducting nerve fibers which convey impulses toward the brain) and efferent pathway 21 (outward conducting nerve fibers which convey impulses to an effector). The vagus nerve is composed of 80% afferent sensory fibers carrying information to the brain from the head, neck, thorax, and abdomen. The sensory afferent cell bodies of the vagus reside in the nodose ganglion and relay information to the nucleus tractus solitarius (NTS) 14.

As shown schematically in FIGS. 1A and 1D, the nucleus of the solitary tract relays this incoming sensory information to the rest of the brain through three main pathways; (1) an autonomic feedback loop, (2) direct projection to the reticular formation in the medulla, and (3) ascending projections to the forebrain largely through the parabrachial nucleus (PBN) 20 and the locus ceruleus (LC) 22. The PBN 20 sits adjacent to the nucleus LC 22 (FIG. 1A). The PBN/LC 20/22 sends direct connections to every level of the forebrain, including the hypothalamus 26, and several thalamic 25 regions that control the insula and orbitofrontal 28 and prefrontal cortices. Perhaps important for mood regulation, the PBN/LC 20/22 has direct connections to the amygdala 29 and the bed nucleus of the stria terminalis—structures that are implicated in emotion recognition and mood regulation.

In sum, incoming sensory (afferent) connections of the vagus nerve 54 provide direct projections to many of the brain regions implicated in nueropsychiatric disorders. These connections reveal how vagus nerve stimulation is a portal to the brainstem and connected regions. These circuits likely account for the neuropsychiatric effects of vagus nerve stimulation.

Increased activity of the vagus nerve is also associated with the release of more serotonin in the brain. Much of the pharmacologic therapy for treatment of migraines is aimed at increasing the levels of serotonin in the brain. Therefore, non-pharmacologic therapy of electrically stimulating the vagus nerve would have benefits for adjunct treatment of migraines and other ailments, such as obsessive compulsive disorders, that would benefit from increasing the level of serotonin in the brain.

The vagus nerve provides an easily accessible, peripheral route to modulate central nervous system (CNS) function. Other cranial nerves can be used for the same purpose, but the vagus nerve is preferred because of its easy accessibility. In the human body there are two vagal nerves (VN), the right VN and the left VN. Each vagus nerve is encased in the carotid sheath along with the carotid artery and jugular vein. The innervation of the right and left vagal nerves is different. The innervation of the right vagus nerve is such that stimulating it results in profound bradycardia (slowing of the heart rate). The left vagal nerve has some innervation to the heart, but mostly innervates the visceral organs such as the gastrointestinal tract. It is known that stimulation of the left vagal nerve does not cause any significant deleterious side effects.

Complex partial seizure is a common form of epilepsy, and some 30–40% of patients afflicted with this disorder are not well controlled by medications. Some patients have epileptogenic foci that may be identified and resected; however, many patients remain who have medically resistant seizures not amenable to resective surgery. Stimulation of the vagus nerve has been shown to reduce or abort seizures in experimental models. Early clinical trials have suggested that vagus nerve stimulation has beneficial effects for complex partial seizures and generalized epilepsy in humans. In addition, intermittent vagal stimulation has been relatively safe and well tolerated during the follow-up period available in these groups of patients. The minimal side effects of tingling sensations and brief voice abnormalities have not been distressing.

Most nerves in the human body are composed of thousands of fibers, of different sizes designated by groups A, B and C, which carry signals to and from the brain. The vagus nerve, for example, may have approximately 100,000 fibers of the three different types, each carrying signals. Each axon (fiber) of that nerve conducts only in one direction, in normal circumstances. The A and B fibers are myelinated (i.e., have a myelin sheath, constituting a substance largely composed of fat), whereas the C fibers are unmyelinated.

A commonly used nomenclature for peripheral nerve fibers, using Roman and Greek letters, is given in the table below,

| Group | External Diameter (μm) | Conduction Velocity (m/sec) |
| --- | --- | --- |
| Myelinated Fibers | | |
| Aα or IA | 12–20 | 70–120 |
| Aβ: IB | 10–15 | 60–80 |
| II | 5–15 | 30–80 |
| Aγ | 3–8 | 15–40 |
| Aδ or III | 3–8 | 10–30 |
| B | 1–3 | 5–15 |
| Unmyelinted fibers | | |
| C or IV | 0.2–1.5 | 0.5–2.5 |

The diameters of group A and group B fibers include the thickness of the myelin sheaths. Group A is further subdivided into alpha, beta, gamma, and delta fibers in decreasing order of size. There is some overlapping of the diameters of the A, B, and C groups because physiological properties, especially the form of the action potential, are taken into consideration when defining the groups. The smallest fibers (group C) are unmyelinated and have the slowest conduction rate, whereas the myelinted fibers of group B and group A exhibit rates of conduction that progressively increase with diameter. Group B fibers are not present in the nerves of the limbs; they occur in white rami and some cranial nerves.

Compared to unmyelinated fibers, myelinated fibers are typically larger, conduct faster, have very low stimulation thresholds, and exhibit a particular strength-duration curve or respond to a specific pulse width versus amplitude for stimulation. The A and B fibers can be stimulated with relatively narrow pulse widths, from 50 to 200 microseconds (μs), for example. The A fiber conducts slightly faster than the B fiber and has a slightly lower threshold. The C fibers are very small, conduct electrical signals very slowly, and have high stimulation thresholds typically requiring a wider pulse width (300–1,000 μs) and a higher amplitude for activation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

The vagus nerve is composed of somatic and visceral afferents (i.e., inward conducting nerve fibers which convey impulses toward the brain) and efferents (i.e., outward conducting nerve fibers which convey impulses to an effector). Usually, nerve stimulation activates signals in both directions (bi-directionally). It is possible, however, through the use of special electrodes and waveforms, to selectively stimulate a nerve in one direction only (unidirectionally). The vast majority of vagal nerve fibers are C fibers, and a majority are visceral afferents having cell bodies lying in masses or ganglia in the skull. The central projections terminate largely in the nucleus of the solitary tract which sends fibers to various regions of the brain (e.g., the hypothalamus, thalamus, and amygdala).

The basic premise of vagal nerve stimulation for control of seizures is that vagal visceral afferents have a diffuse central nervous system (CNS) projection, and activation of these pathways has a widespread effect on neuronal excitability.

The cervical component of the vagus nerve (10 th cranial nerve) transmits primarily sensory information that is important in the regulation of autonomic activity by the parasympathetic system. General visceral afferents constitute approximately 80% of the fibers of the nerve, and thus it is not surprising that vagal nerve stimulation (VNS) can profoundly affect CNS activity. With cell bodies in the nodose ganglion, these afferents originate from receptors in the heart, aorta, lungs, and gastrointestinal system and project primarily to the nucleus of the solitary tract which extends throughout the length of the medulla oblongata. A small number of fibers pass directly to the spinal trigeminal nucleus and the reticular formation.

As might be predicted from the electrophysiologic studies, the nucleus of the solitary tract has widespread projection to cerebral cortex, basal forebrain, thalamus, hypothalamus, amygdala, hippocampus, dorsal raphe, and cerebellum as shown in FIG. 1D (from Epilepsia, vol. 3, suppl. 2: 1990, page S2).

Even though observations on the profound effect of electrical stimulation of the vagus nerve on central nervous system (CNS) activity, extends back to the 1930's, in the mid-1980s it was suggested that electrical stimulation of the vagus nerve might be effective in preventing seizures. Early studies on the effects of vagal nerve stimulation (VNS) on brain function focused on acute changes in the cortical electroencephalogram (EEG) of anesthetized animals. Investigators found that VNS could temporarily synchronize or desynchronize the electroencephalogram, depending on the level of anesthesia and the frequency or intensity of the vagal stimulus. These observations had suggested that VNS exerted its anticonvulsant effect by desynchronizing cortical electrical activity. However, subsequent clinical investigations have not shown VNS-induced changes in the background EEGs of humans. A study, which used awake and freely moving animals, also showed no VNS-induced changes in background EEG activity. Taken together, the findings from animal study and recent human studies indicate that acute desynchronization of EEG activity is not a prominent feature of VNS when it is administered during physiologic wakefulness and sleep, and does not explain the anticonvulsant effect of VNS.

The mechanism by which vagal nerve stimulation (VNS) exerts its influence on seizures is not entirely understood. An early hypotheses had suggested that VNS utilizes the relatively specific projection from the nucleus of the solitary track to limbic structures to inhibit partial seizures, particularly those involving cortex, which regulates autonomic activity or visceral sensations such as in temporal lobe epilepsy. Afferent VNS at the onset of a partial seizure could abort the seizure in the same way somatosensory stimuli can abort a seizure from the rolandic cortex; however, chronic intermittent stimulation may also produce an alteration in limbic circuitry that outlasts the stimulus and decreases epileptogenesis or limits seizure spread. Support for this hypothesis comes from studies of fos immunoreactivity in the brain of rats in response to VNS. Fos is a nuclear protein resulting from expression of early immediate genes in highly active neurons. VNS causes a specific fos immunolabeling in amygdala and limbic neocortex, suggesting that the antiepileptic effect may be mediated in these areas. Such activation of genetic mechanisms could account for the apparent sustained antiepileptic effect of intermittent stimulation.

Another possible mechanism that is being explored to explain an antiseizure effect of VNS is activation of the brainstem noradrenergic nuclei, locus ceruleus and A5, which also show fos immunolabeling. Noradrenergic mechanisms are well known to influence seizure activity in genetic epilepsy-prone rats, and the anticonvulsant effects of VNS against maximal electroshock seizures can be blocked inactivation of the loc. ceruleus. Woodbury and Woodbury (1990) suggested that VS acts through increasing release of glycine or GABA since seizures induced by both PTZ and strychnine can be blocked by VNS. Other neurotransmitter systems may also be implicated since VNS increases cerebrospinal fluid homovanilic acid and 5-hydroxyindoleacetate, suggesting modulation of dopaminergic and serotonergic systems. Finally, a nonspecific alteration of activity in the brainstem reticular system with subsequent arousal must be considered.

VNS appears to have similar efficacy in both partial and generalized seizures in experimental models and in human epilepsy consistent with a nonspecific effect. Furthermore, the same inhibition of interictal corticalspike activity as seen with VNS occurs in animals during electrical stimulation of the midbrain reticular formation or with thermal stimulation of somatosensory nerves in the rat tail. Reduction of experimental generalized spike wave by arousal has also been documented. Similarly, nonspecific afferent stimulation has been well demonstrated in humans to suppress focal spikes, generalized spike waves, and seizures.

VNS may inhibit seizures directly at the level of cerebral cortical neuronal irritability, or at the level of diffuse ascending subcortical projection systems, or both. Thus, VNS is also well suited for the treatment of medication-resistant symptomatic generalized epilepsy (SGE), in which, characteristically both focal and generalized features are found on interictal EEGs and also in clinical seizure types.

Now considering the background of urinary urge incontinence. FIG. 1E shows a sagittal section of the human female pelvis showing the bladder 10 and urethra 13 in relation to other anatomic structures. Urinary continence requires a relaxed bladder during the collecting phase and permanent closure of the urethra, whereas at micturition (urination), an intravesical pressure above the opening pressure of the simultaneously relaxing urethra has to be generated. These functions of the bladder and urethra are centrally coordinated and non-separable. At bladder filling, the sensation of urge is mediated by slowly adapting mechanoreceptors in the bladder wall and the same receptors provide the triggering signal for micturition and the main driving force for a sustained micturition contraction. The mechanoreceptors are, technically speaking, tension receptors. It has been found that they respond equally well to tension increases induced passively by bladder filling and those induced actively by a detrusor 192 (muscle in the wall of the urinary bladder) contraction, as depicted schematically in FIG. 1F. These receptors have high dynamic sensitivity and are easily activated by external pressure transients, as may occur during coughing or tapping of the abdominal wall. Their faithful response to active changes in bladder pressure is well illustrated.

When sufficiently activated, the mechanoreceptors trigger a coordinated micturition reflex via a center in the upper pons 188, (FIG. 1F). The reflex detrusor 192 contraction generates an increased bladder pressure and an even stronger activation of the mechanoreceptors. Their activity in turn reinforces the pelvic motor output to the bladder, which leads to a further increase in pressure and more receptor activation and so on. In this way, the detrusor contraction is to a large extent self generating once initiated. Such a control mechanism usually is referred to as a positive feedback, and it may explain the typical all-or-nothing behavior of the parasympathetic motor output to the bladder. Once urine enters the urethra, the contraction is further enhanced by reflex excitation from urethral receptors. Quantitatively, the bladder receptors are most important.

A great advantage of the positive feedback system is that it ascertains a complete emptying of the bladder during micturition. As long as there is any fluid left in the lumen, the intravesical pressure will be maintained above the threshold for the mechanoreceptors and thus provide a continuous driving force for the detrusor. A drawback with this system is that it can easily become unstable. Any stimulus that elicits a small burst of impulses in mechanoreceptor afferents may trigger a full-blown micturition reflex. To prevent this from happening during the filling phase, the neuronal system controlling the bladder is equipped with several safety devices both at the spinal and supraspinal levels.

The best-known spinal mechanism is the reflex control of the striated urethral sphincter 190, which increases its activity in response to bladder mechanoreceptor activation during filling. An analogous mechanism is Edvardsen's reflex, which involves mechanoreceptor activation of inhibitory sympathetic neurons to the bladder. The sympathetic efferents have a dual inhibitory effect, acting both at the postganglionic neurons in the vesical ganglia and directly on the detrusor muscle 192 of the bladder. The sphincter and sympathetic reflexes are automatically turned off at the spinal cord level during a normal micturition. At the supraspinal level, there are inhibitory connections from the cerebral cortex and hypothalamus to the pontine micturition center. The pathways are involved in the voluntary control of continence. Other inhibitory systems seem to originate from the pontine and medullary parts of the brainstem with at least partly descending connections.

Bladder over-activity and urinary urge incontinence may result from an imbalance between the excitatory positive feedback system of the bladder 10 and inhibitory control systems causing a hyperexcitable voiding reflex. Such an imbalance may occur after macroscopic lesions at many sites in the nervous system or after minor functional disturbances of the excitatory or inhibitory circuits. Urge incontinence due to detrusor instability seldom disappears spontaneously. The symptomatic pattern also usually is consistent over long periods.

Based on clinical experience, subtypes of urge incontinence include, Phasic detrusor instability and uninhibited overactive bladder. Phasic detrusor instability is characterized by normal or increased bladder sensation, phasic bladder contractions occurring spontaneously during bladder filling or on provocation, such as by rapid filling, coughing, or jumping. This condition results from a minor imbalance between the bladder's positive-feedback system and the spinal inhibitory mechanisms. Uninhibited overactive bladder is characterized by loss of voluntary control of micturition and impairment of bladder sensation. The first sensation of filling is experienced at a normal or lowered volume and is almost immediately followed by involuntary micturition. The patient does not experience a desire to void until she/he is already voiding with a sustained detrusor contraction and a concomitant relaxation of the urethra, i.e., a well-coordinated micturition reflex. At this stage, she/he is unable to interrupt micturition voluntarily. The sensory disturbance of these subjects is not in the periphery, at the level of bladder mechanoreceptors, as the micturition reflex occurs at normal or even small bladder volumes. More likely, the suprapontine sensory projection to the cortex is affected. Such a site is consistent with the coordinated micturition and the lack of voluntary control. The uninhibited overactive bladder is present in neurogenic dysfunction.

Since bladder over-activity results from defective central inhibition, it seems logical to improve the situation by reinforcing some other inhibitory system. Patients with stress and urge incontinence are difficult to treat adequately. Successful therapy of the urge component does not influence the stress incontinence. While an operation for stress incontinence sometimes results in deterioration of urgency. Electrostimulation is a logical alternative in mixed stress and urge incontinence, since the method improves urethral closure as well as bladder control. Drug treatment often is insufficient and, even when effective, does not lead to restoration of a normal micturition pattern.

Neuromodulation is a technique that uses electrical stimulation of the sacral nerves, (a general diagram of spinal cord and sacral nerves 185 is shown in FIG. 2). The aim of this treatment modality is to achieve detrusor 192 inhibition by chronic electrical stimulation of afferent somatic sacral nerve fibers 185 via implanted electrodes coupled to a subcutaneously placed pulse generation means.

The rationale of this treatment modality is based on the existence of spinal inhibitory systems that are capable of interrupting a detrusor 192 contraction. Inhibition can be achieved by electrical stimulation of afferent anorectal branches of the pelvic nerve, afferent sensory fibers in the pudendal nerve and muscle afferents from the limbs. Most of these branches and fibers reach the spinal cord via the dorsal roots of the sacral nerves 185. Of the sacral nerve roots the S3 root is the most practical for use in chronic electrical stimulation. In neuromodulation, the entire innervation system should be intact. As shown schematically in FIG. 3, the procedure consists of placing electrodes 161,162 in one of the sacral foraman as close to the pelvic plexus and pudendal nerve as possible and connecting the lead 159 with a means for electrical stimulation 149. The hypothesis behind neuromodulation of the sacral roots (sensory and motor) is to correct, by the use of regulating electrical impulses, the dys-synergic activities of the cholinergic, adrenergic, and motor reflex pathways that initiate vesical storage and micturition. Although some theories have been developed that explain the effects of neuromodulation, most of the results are based on empiric findings in human studies. Some animal experiments and electrophysiologic studies in humans show there is a spinal inhibitory action through the afferent branches of the pelvic and pudendal nerves. It is not clear whether neuromodulation primarily influences the micturiction center located near the thalamus 25. Some maintain that there is a direct correction of the dys-synergis of the pelvic floor (pudendal nerve) by influencing the abnormal contractility of the pelvic floor.

A neurophysiological explanation for the effectiveness of this treatment modality in detrusor instability is based on animal experiments and electrophysiological studies in humans. Electrical stimulation for the treatment of urinary incontinence has evolved over the past 40 years. The mechanism of action of electrical stimulation was investigated initially in animal models. Over 100 years ago, Griffiths demonstrated relaxation of a contracted detrusor during stimulation of the proximal pudendal nerve in the cat model and further work clarified the role of pudendal afferents in relation of the detrusor. Spinal inhibitory systems capable of interrupting a detrusor contraction can be activated by electrical stimulation of afferent anorectal branches of the pelvic nerve, afferent sensory fibers in the pudendal nerve and muscle afferents from the limbs. The effectiveness of neuromodulation in humans has been objectively demonstrated by urodynamic improvement, especially in light of the fact that such effects have not been noted in drug trials.

Neuromodulation also acts on neural reflexes but does so internally by stimulation of the sacral nerves 185. Sacral nerve 185 stimulation is based on research dedicated to the understanding of the voiding reflex as well as the role and influence of the sacral nerves 185 on voiding behavior. This research led to the development of a technique to modulate dysfunctional voiding behavior through sacral nerve stimulation. It is thought that sacral nerve stimulation induces reflex mediated inhibitory effects on the detrusor through afferent and/or efferent stimulation of the sacral nerves 185.

Even though the precise mechanism of action of electrical stimulation in humans is not fully understood, it has been shown that sensory input traveling through the pudendal nerve can inhibit detrusor activity in humans. Most experts believe that non-implanted electrical stimulation works by stimulating the pudendal nerve afferents, with the efferent outflow causing contraction of the striated pelvic musculature. There is also inhibition of inappropriate detrusor activity, though the afferent mechanism has yet to be clarified. There is consensus that the striated musculature action is able to provide detrusor inhibition in this setting, though data supporting this hypotheses are lacking. In summary, the rationale for neuromodulation in the management of such patients is the observation that stimulation of the sacral nerves via electrical stimulation can inhibit inappropriate neural reflex behavior.

PRIOR ART

One type of prior art non-pharmacological therapy for neurologic, neuropsychiatric, and urologic disorders is generally directed to the use of an implantable lead and an implantable pulse generator technology or "cardiac pacemaker-like" technology. In these applications, the pulse generator is programmed via a personnel computer (PC) based programmer that is modified and adapted with a programmer wand which is placed on top of the skin over the pulse generator implant site. Each parameter is programmed independent of the other parameters. Therefore, millions of different combinations of programs are possible. In the current application, a limited number of programs are pre-selected. The library of pre-packaged programs can be any number, say 100, and such a number is considered within the scope of this invention. For patient convenience , the presently preferred embodiment contains nine pre-determined programs.

U.S. Pat. No. 3,796,221 (Hagfors) is directed to controlling the amplitude, duration and frequency of electrical stimulation applied from an externally located transmitter to an implanted receiver by inductively coupling. Electrical circuitry is schematically illustrated for compensating for the variability in the amplitude of the electrical signal available to the receiver because of the shifting of the relative positions of the transmitter-receiver pair. By highlighting the difficulty of delivering consistent pulses, this patent points away from applications such as the current application, where consistent therapy needs to be continuously sustained over a prolonged period of time (24 hours a day for years). The methodology disclosed is focused on circuitry within the receiver, which would not be sufficient when the transmitting coil and receiving coil assume significantly different orientation, which is likely in the current application. The present invention discloses a novel approach for this problem.

U.S. Pat. No. 5,304,206 (Baker, Jr. et al) is directed to activation techniques for implanted medical stimulators. The system uses either a magnet to activate the reed switch in the device, or tapping which acts through the piezoelectric sensor mounted on the case of the implanted device, or a combination of magnet and tapping sequence.

U.S. Pat. Nos. 4,702,254, 4,867,164 and 5,025,807 (Zabara) generally disclose animal research and experimentation related to epilepsy and the like and are directed to stimulating the vagus nerve by using pacemaker technology, such as an implantable pulse generator. These patents are based on several key hypotheses, some of which have since been shown to be incorrect. The pacemaker technology concept consists of a stimulating lead connected to a pulse generator (containing the circuitry and DC power source) implanted subcutaneously or submuscularly, somewhere in the pectoral or axillary region, with an external personal computer (PC) based programmer. Once the pulse generator is programmed for the patient, the fully functional circuitry and power source are fully implanted within the patient's body. In such a system, when the battery is depleted, a surgical procedure is required to disconnect and replace the entire pulse generator (circuitry and power source). These patents neither anticipate practical problems of an inductively coupled system for adjunct therapy of epilepsy, nor suggest solutions to the same for an inductively coupled system for adjunct therapy of partial complex or generalized epilepsy.

U.S. Pat. No. 5,299,569 (Wernicke et al.) is directed to the use of implantable pulse generator technology for treating and controlling neuropsychiatric disorders including schizophrenia, depression, and borderline personality disorder.

U.S. Pat. No. 5,540,734 (Zabara) is directed to stimulation of one or both of a patient's trigeminal and glossopharyngeal nerve utilizing an implanted pulse generator.

U.S. Pat. No. 4,771,779 (Tanagho et al) is directed to a system for controlling bladder evacuation, which consists of multiple implanted stimulation systems having electrodes positioned on nerves controlling external sphincter and bladder functions, and electronic control system which transmit to the stimulation systems. In this patent, by having multiple stimulation systems and means of controlling them, the interaction between stimulating the bladder and external sphincter can be controlled.

An implantable pulse generator and lead with a PC based external programmer is specifically advantageous for cardiac pacing applications for several reasons, including:

1) A cardiac pacemaker must sense the intrinsic activity of the heart, because cardiac pacemakers deliver electrical output primarily during the brief periods when patients either have pauses in their intrinsic cardiac activity or during those periods of time when the heart rate drops (bradycardia) below a certain pre-programmed level. Therefore, for most of the time, in majority of patients, the cardiac pacemaker "sits" quietly monitoring the patient's intrinsic cardiac activity.

2) The stimulation frequency for cardiac pacing is typically close to 1 Hz, as opposed to approximately 20 Hz or higher, typically used in nerve stimulation applications.

3) Patients who require cardiac pacemaker support are typically in their 60's, 70's or 80's years of age.

The combined effect of these three factors is that the battery in a pacemaker can have a life of 10–15 years. Most patients in whom a pacemaker is indicated are implanted only once, with perhaps one surgical pulse generator replacement.

In contrast, patients with neurological and urological disorders in whom electrical stimulation is beneficial are much younger as a group. Also, stimulation frequency is typically 20 Hz or higher, and the total stimulation time per day is much longer than is typical or cardiac pacemakers. As a result, battery drain is typically much higher for nerve stimulation applications than for cardiac pacemakers.

The net result of these factors is that the battery will not last nearly as long as in cardiac pacemakers. Because the indicated patient population is also much younger, the expense and impact of surgical generator replacement will become significant, and detract from the appeal of this therapy. In fact, it has been reported in the medical literature that the battery life can be as short as one and half years for implantable nerve stimulator. (R. S McLachlan, p. 233).

There are several other advantages of the present inductively coupled system.

1) The hardware components implanted in the body are much less. This is specifically advantageous for the patient in terms of patient comfort, and it decreases the chances of the hardware getting infected in the body. Typically, when an implantable system gets infected in the body, it cannot be easily treated with antibiotics and eventually the whole implanted system has to be explanted.

2) Because the power source is external, the physician can use stimulation sequences that are more effective and more demanding on the power supply, such as longer "on" time.

3) With the controlling circuitry being external, the physician and the patient may easily select from a number of predetermined programs, override a program, manually operate the device or even modify the predetermined programs.

4) The external inductively-coupled nerve stimulation (EINS) system is quicker and easier to implant.

5) The external pulse generator does not need to be monitored for "End-of-Life" (EOL) like the implantable system, thus resulting in cost saving and convenience.

6) The EINS system can be manufactured at a significantly lower cost of an implantable pulse generator and programmer system, providing the patient and medical establishment with cost effective therapies.

7) The EINS system makes it more convenient for the patient or caretaker to turn the device on during an "Aura" that sometimes precedes the seizures. Also, because programming the device is much simpler, the patient or caretaker may reprogram the device at night time by simply pressing one or two buttons to improve patient comfort.

8. Occasionally, an individual responds adversely to an implanted medical device and the implanted hardware must be removed. In such a case, a patient having the EINS systems has less implanted hardware to be removed and the cost of the pulse generator does not become a factor.

SUMMARY OF THE INVENTION

The external pulse generator of this invention contains a primary coil and is adapted to be coupled to an implanted lead-receiver for neuromodulation treatment of neurological, neuropsychiatric, and urological disorders. The disorders that are amenable to this type of therapy include severe depression, migraine, partial complex epilepsy, generalized epilepsy, involuntary movement disorders, dementia including Alzheimer's disease, obsessive compulsive disorders, urinary incontinence and bladder control. The adjunct (add-on) treatment of the specific therapy being used depends upon the specific predetermined program being used, along with the nerve bundle being stimulated. Each predetermined program consists of unique combination of pulse amplitude, pulse-width, frequency of stimulation, and on-off time periods.

In one aspect of the invention the pulse generator contains a limited number of predetermined programs packaged into the stimulator, which can be accessed directly without a programmer. The limited number of programs can be any number of programs up to as many as 100 programs, and such a number is considered within the scope of this invention. For convenience and ease of use, the presently preferred embodiment contain nine predetermined programs packaged into the stimulator. Some of these programs may be locked out to the patient or caretaker, and be accessible to the medical personnel only.

In another aspect of the invention, the patient can selectively activate any program within the confines of patient-available programs, or turn the device off.

In yet another aspect of the invention, the pre-packaged programs can be modified with a programming station connected to the pulse generator with a RS232-C serial connection.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

FIG. 21 is a diagram of an electrode containing steroid drug in a silicone collar at the base of electrode.

FIG. 22 is a diagram of an electrode with steroid drug coated on the surface of the electrode.

FIG. 23 is a diagram of cross sections of implantable lead-receiver body showing different lumens.

DESCRIPTION OF THE INVENTION

Figure 1A:
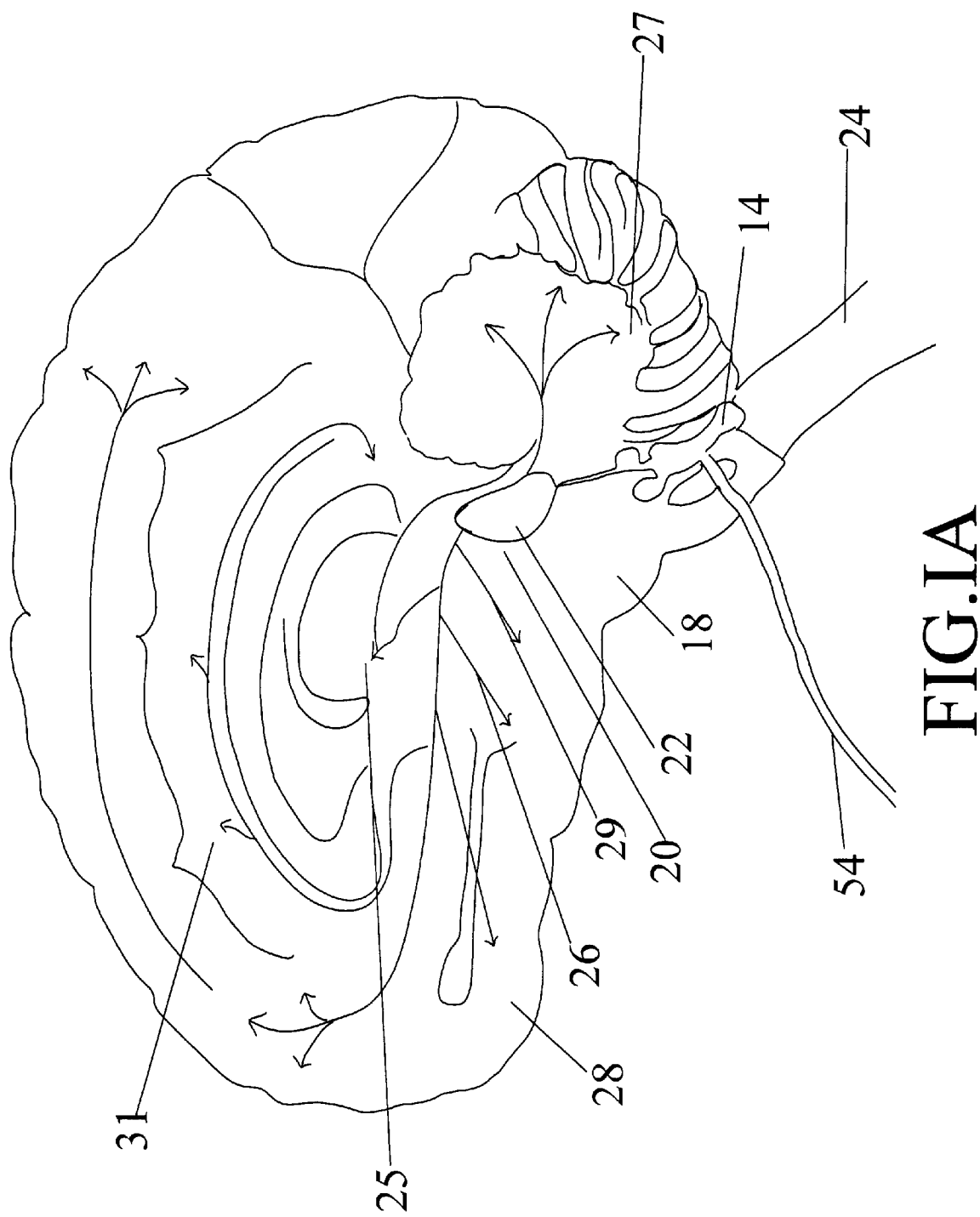
FIG. 1A is a diagram of the lateral view of brain and spinal cord, with its relationship to the vagus nerve.
Figure 1B:
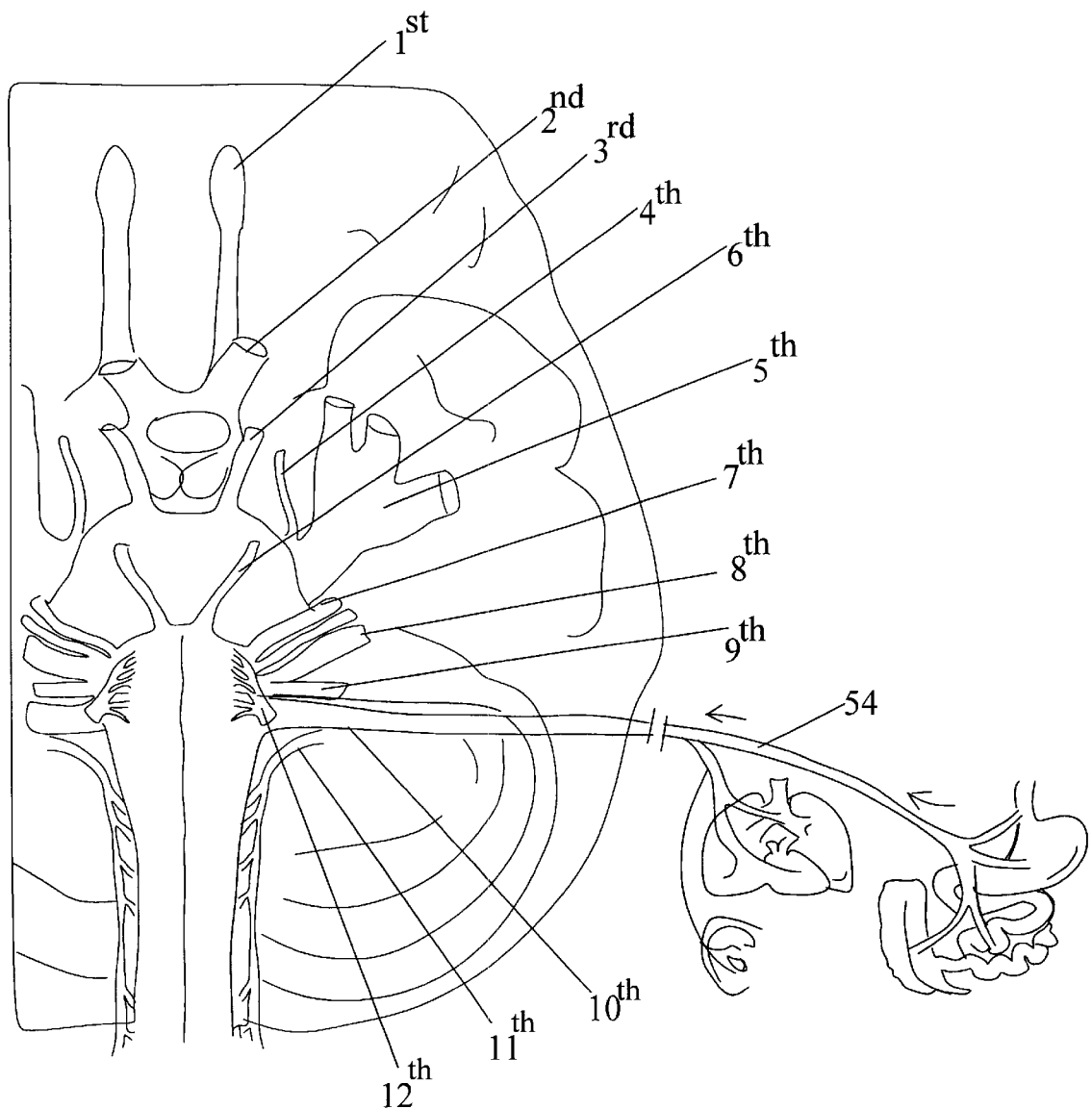
FIG. 1B is a diagram of the base of brain showing the relationship of vagus nerve to the other cranial nerves.
Figure 1C:
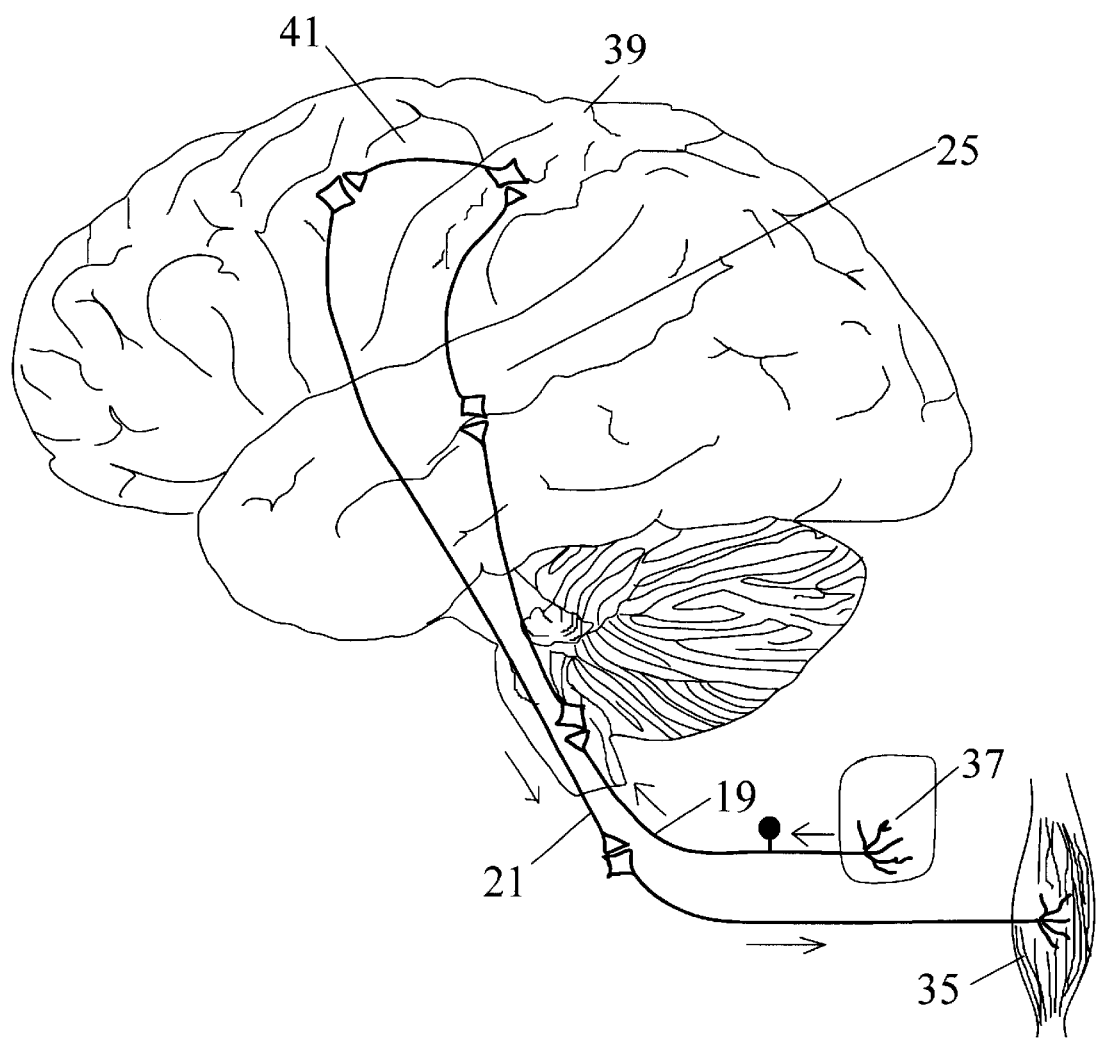
FIG. 1C is a diagram of brain showing afferent and efferent pathways.
Figure 1D:
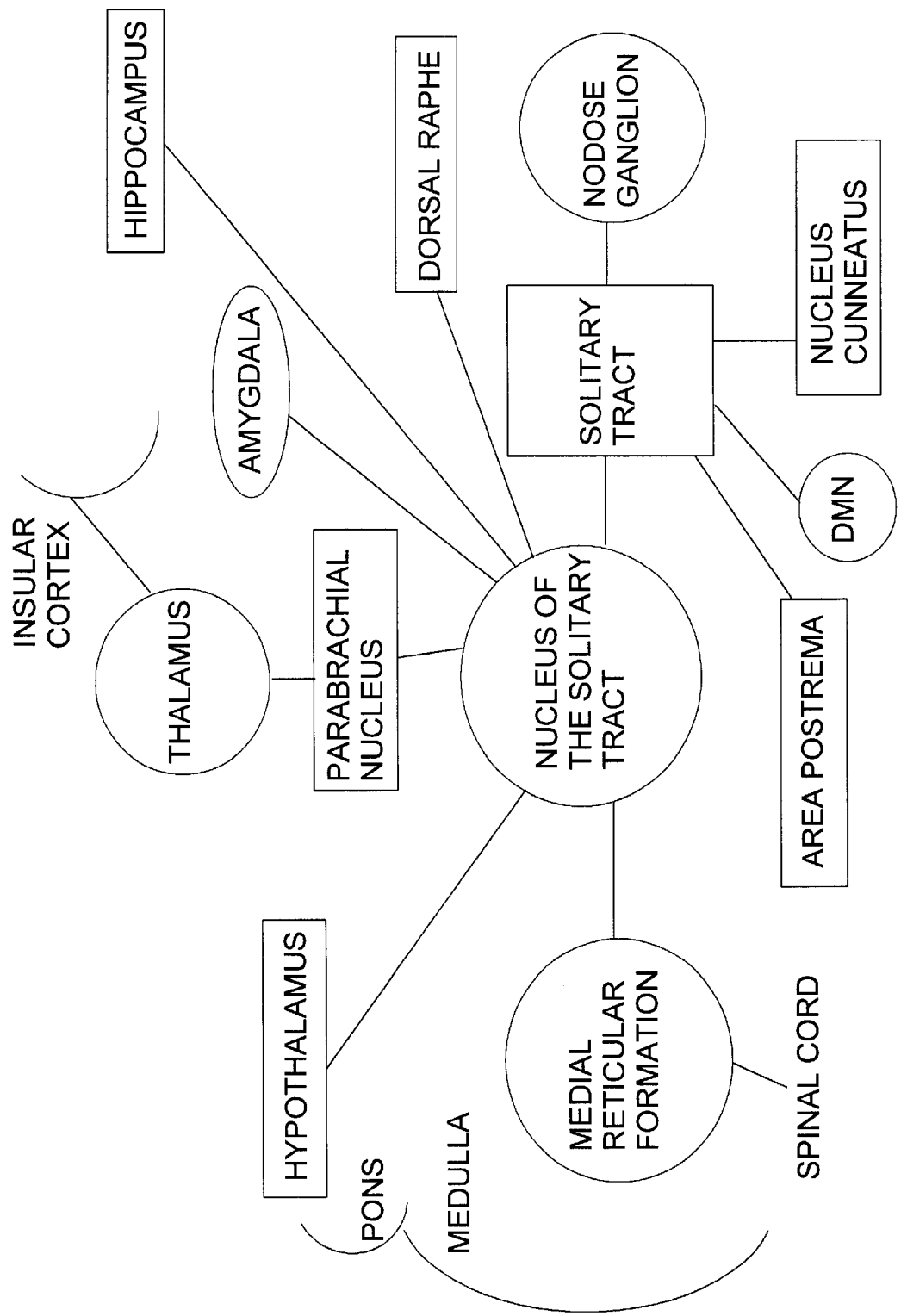
FIG. 1D is diagram of vagal nerve afferents through the nucleus of the solitary tract.
Figure 1E:
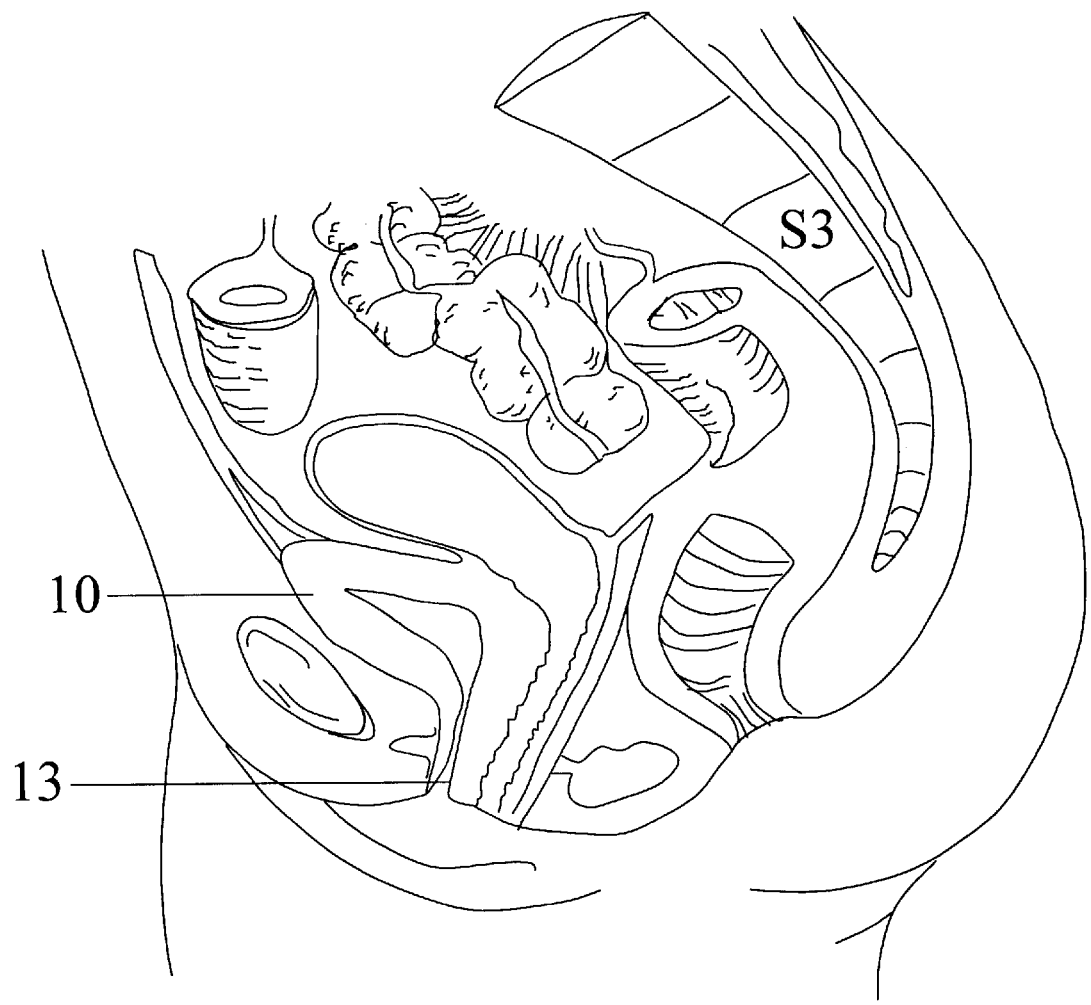
FIG. 1E shows a diagram of the sagittal section of the female pelvis, showing the relationship between various anatomic structures.
Figure 1F:
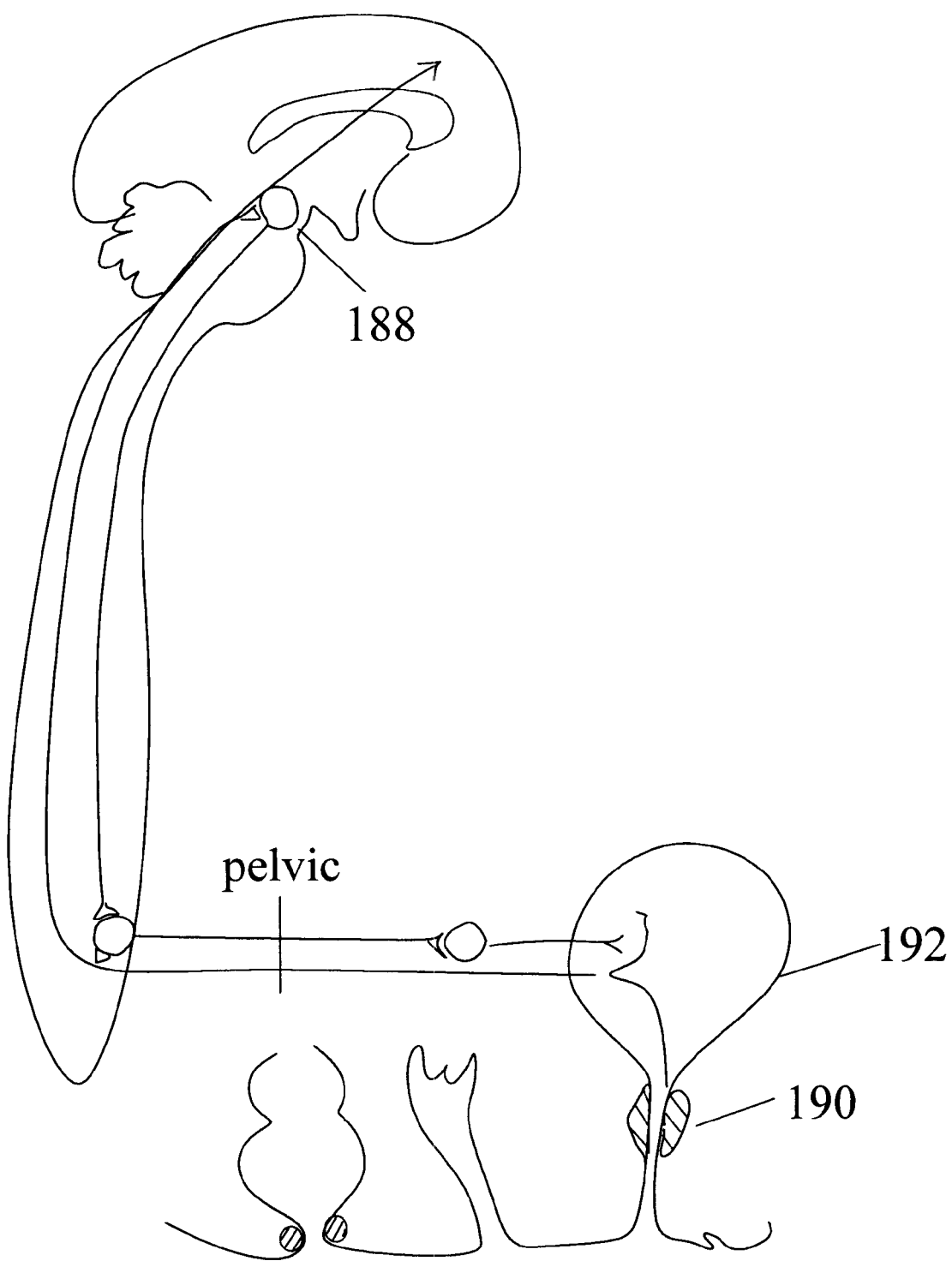
FIG. 1F is a schematic diagram showing physiological control of micturition.
Figure 2:
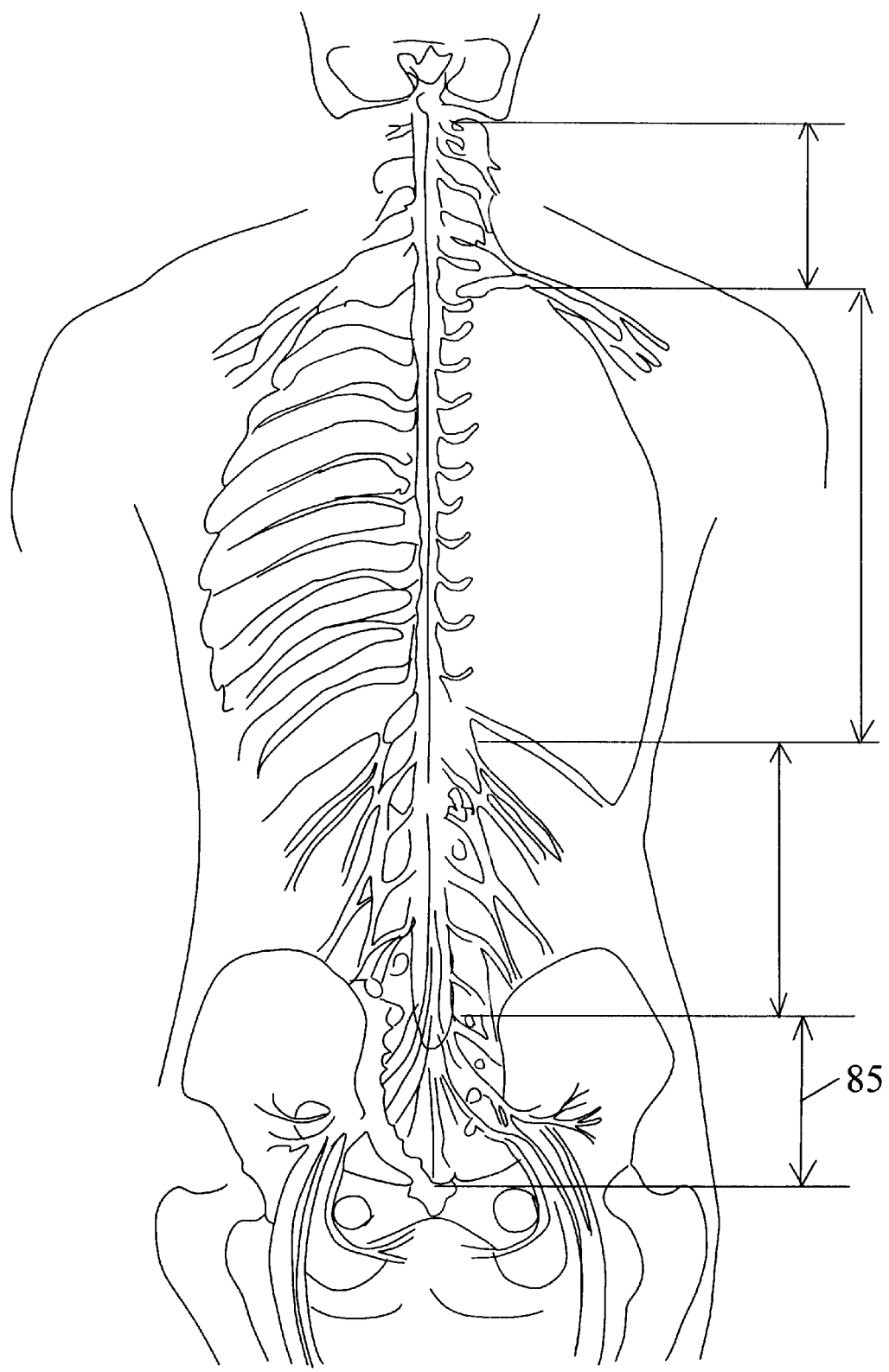
FIG. 2 is a diagram showing anatomic relationships of spinal nerves and sacral plexus.
Figure 3:
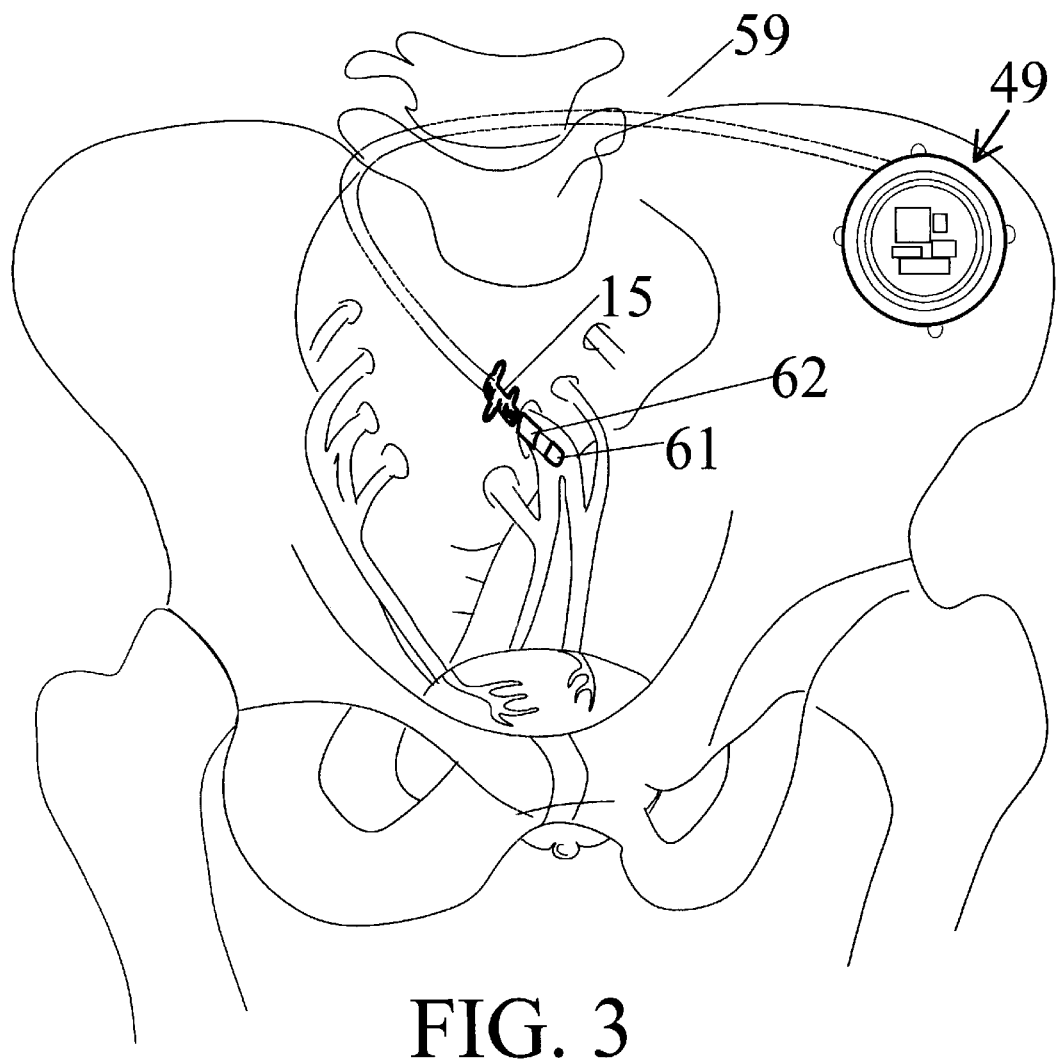
FIG. 3 is a schematic diagram of the sacral region showing electrodes in sacral foraman, and placement of the lead-receiver.
Figure 4:
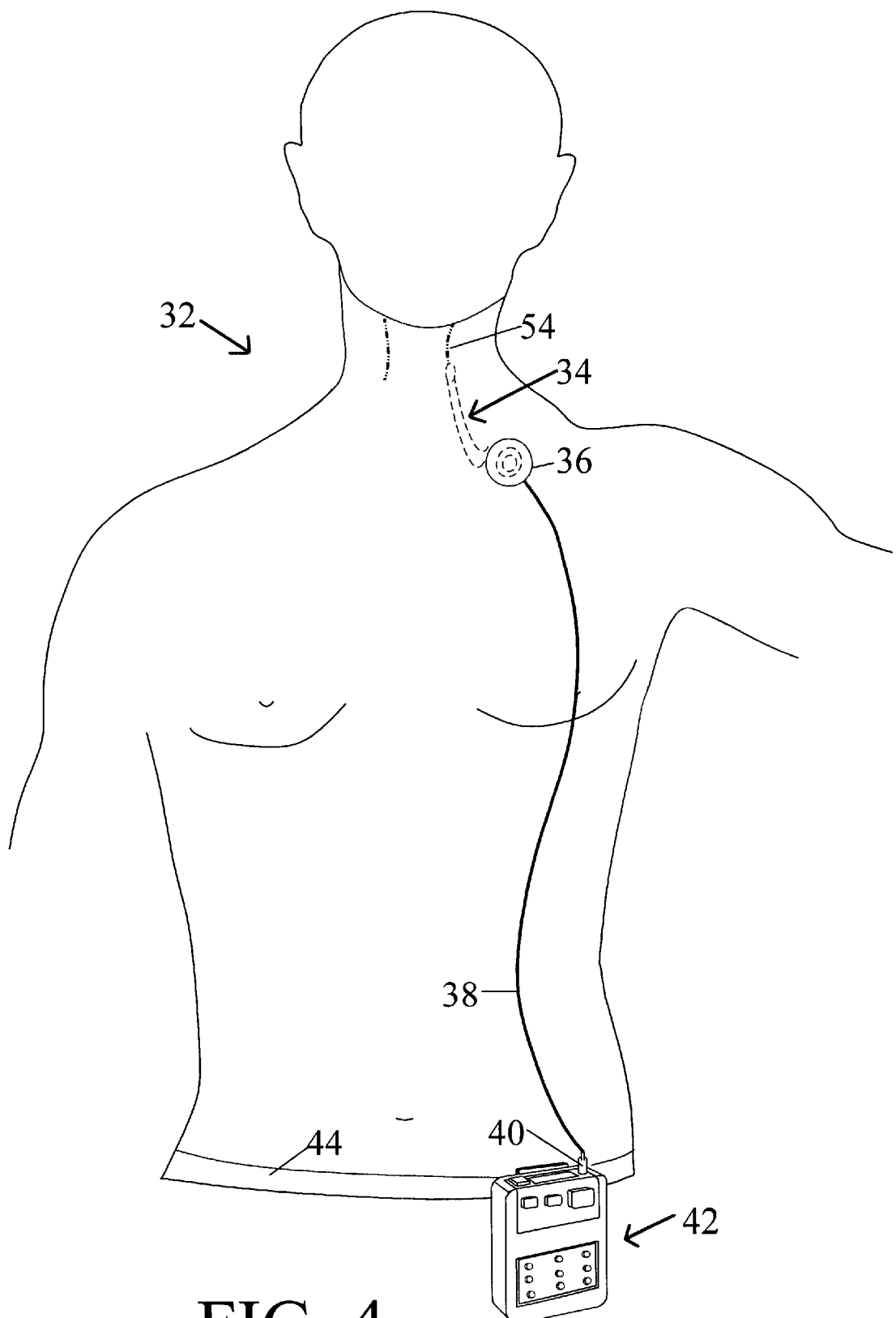
FIG. 4 is a diagram showing a patient wearing an external inductively-coupled nerve stimulator (EINS) system.

FIG. 4 shows a schematic diagram of a patient 32 with an implantable lead-receiver 34 and an external stimulator 42, clipped on to a belt 44 in this case. The external stimulator 42, may alternatively be placed in a pocket or other carrying device. An external patch electrode 36 provides the coupling between the external stimulator 42 and the implantable lead-receiver 34.

Figure 5:
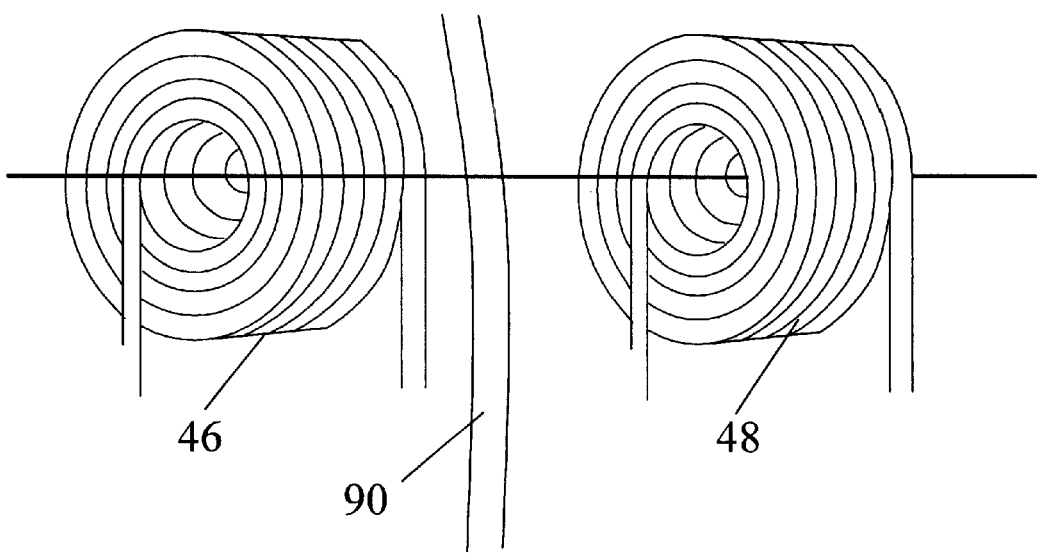
FIG. 5 is a diagram showing two coils along their axis, in a configuration such that the mutual inductance would be maximum.
Figure 8:
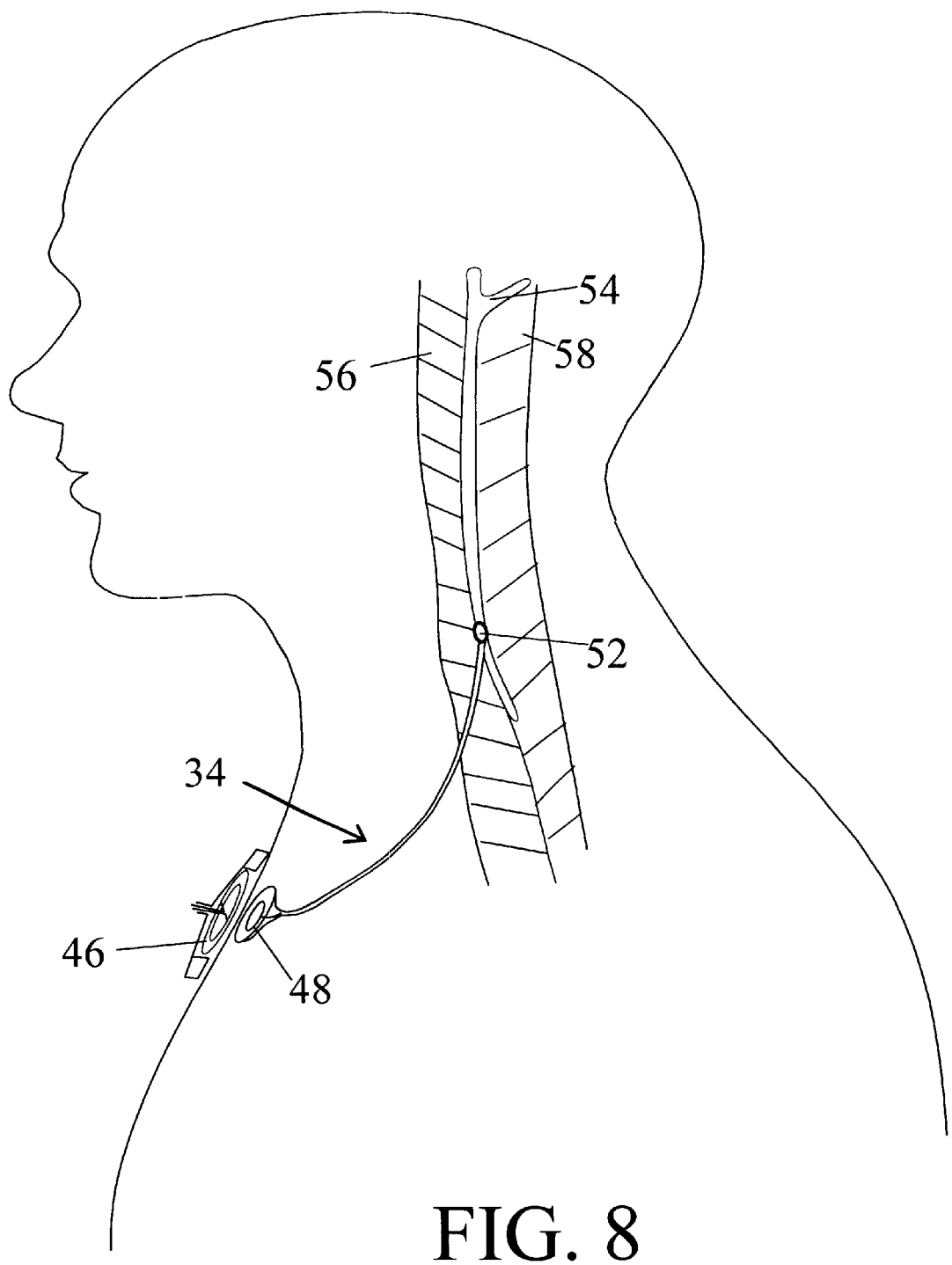
FIG. 8 is a diagram showing the implanted lead-receiver and the transmitting coil.

The external stimulator 42 is inductively coupled to the lead-receiver 34. As shown in FIG. 5, when two coils are arranged with their axes on the same line, current sent through coil 46 creates a magnetic field that cuts coil 48 which is placed subcutaneously. Consequently, a voltage will be induced in coil 48 whenever the field strength of coil 46 is changing. This induced voltage is similar to the voltage of self-induction but since it appears in the second coil because of current flowing in the first, it is a mutual effect and results from the mutual inductance between the two coils. Since these two coils are coupled, the degree of coupling depends upon the physical spacing between the coils and how they are placed with respect to each other. Maximum coupling exists when they have a common axis and are as close together as possible. The coupling is least when the coils are far apart or are placed so their axes are at right angles. As shown in FIG. 8, the coil 48 inside the lead-receiver 34 is approximately along the same axis as the coil 46 in the external skin patch 36.

Figure 6A:
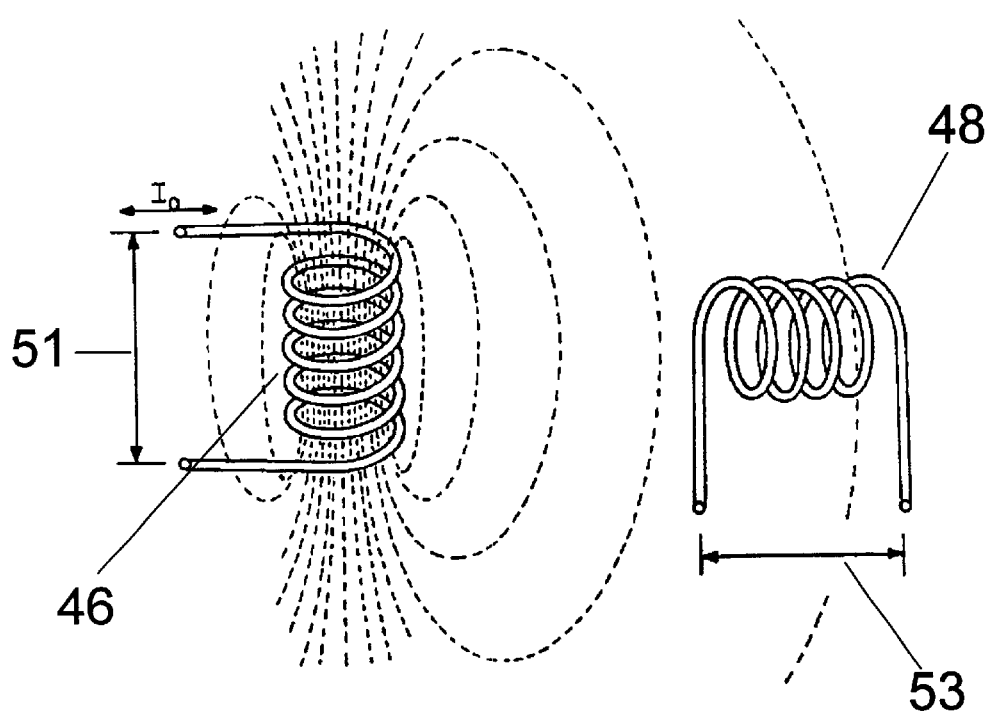
FIG. 6A is a diagram showing the effects of two coils with axes at right angles.
Figure 6B:
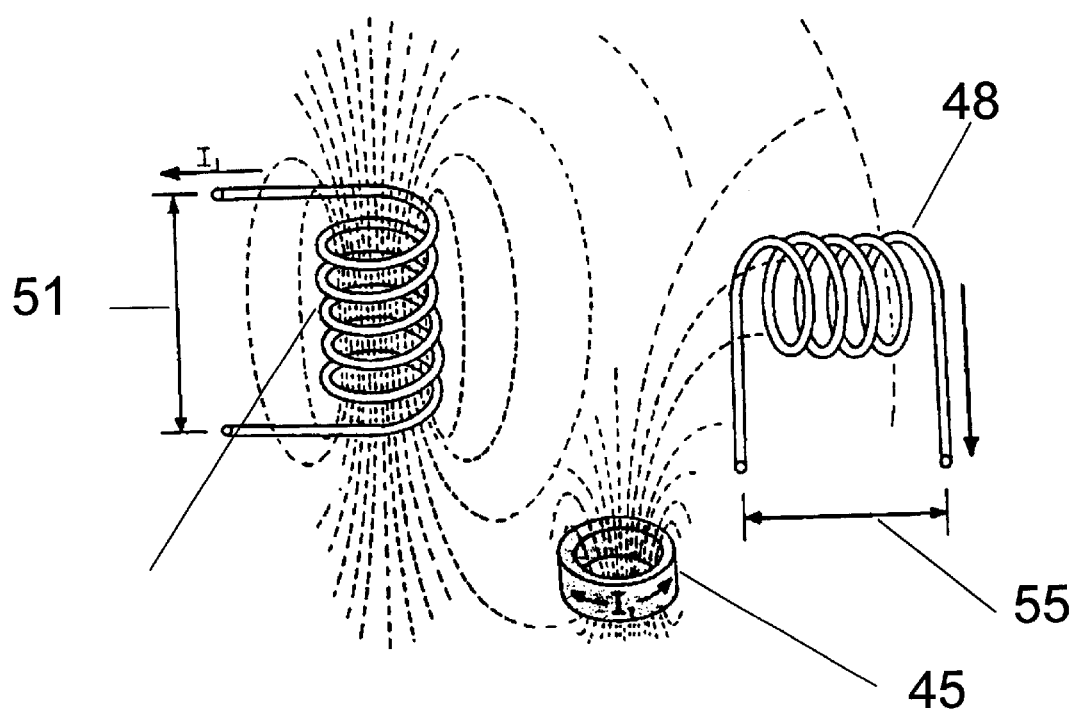
FIG. 6B is a diagram showing the effects of two coils with axes at right angles, with a ferrite target included.
Figure 7A:
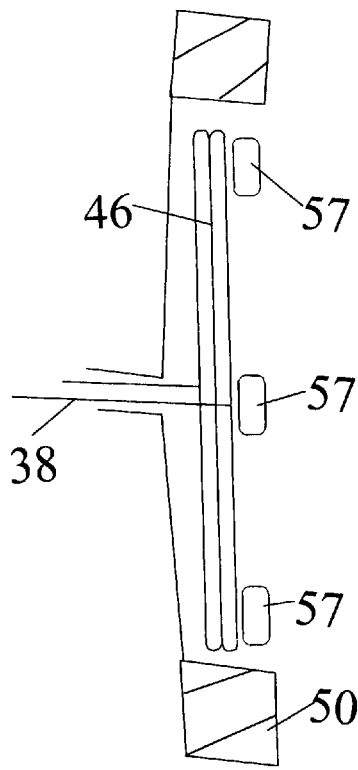
FIG. 7A is a side view of an external patch showing the transmitting coil and targets.
Figure 7B:
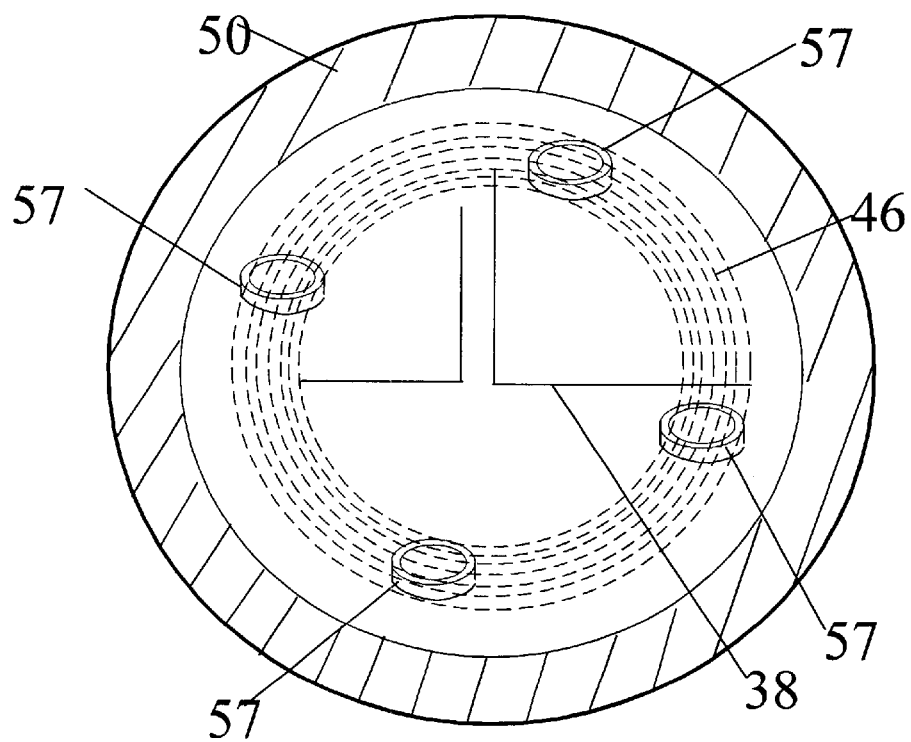
FIG. 7B is top view of an external patch showing the transmitting coil and targets.

As shown in FIG. 6A, when the axis of transmitting coil 46 is at right angles to the axis of the receiving coil 48, a given driving voltage 51 results in zero voltage 53 across the receiving coil 48. But, as shown in FIG. 6B by adding ferrite target 45, a given driving voltage 51 through the transmitting coil 46 results in a signal voltage 55 across the receiver coil 48. The efficiency is improved by having multiple ferrite targets. An alternate external patch shown in FIGS. 7A and 7B contains multiple targets 57. FIG. 7A shows a side view of the patch, and FIG. 7B shows a top view of the patch. Having multiple targets 57 in the external patch 43 compensates for non-alignment of the axis between the transmitting coil 46 and receiving coil 48. Since relative rotations between the axis of external transmitting coil 46 and internal receiving coil 48 which may occur during breathing, muscle contractions, or other artifacts are compensated for, results in continuous prolonged stimulation.

Figures 9, 10:
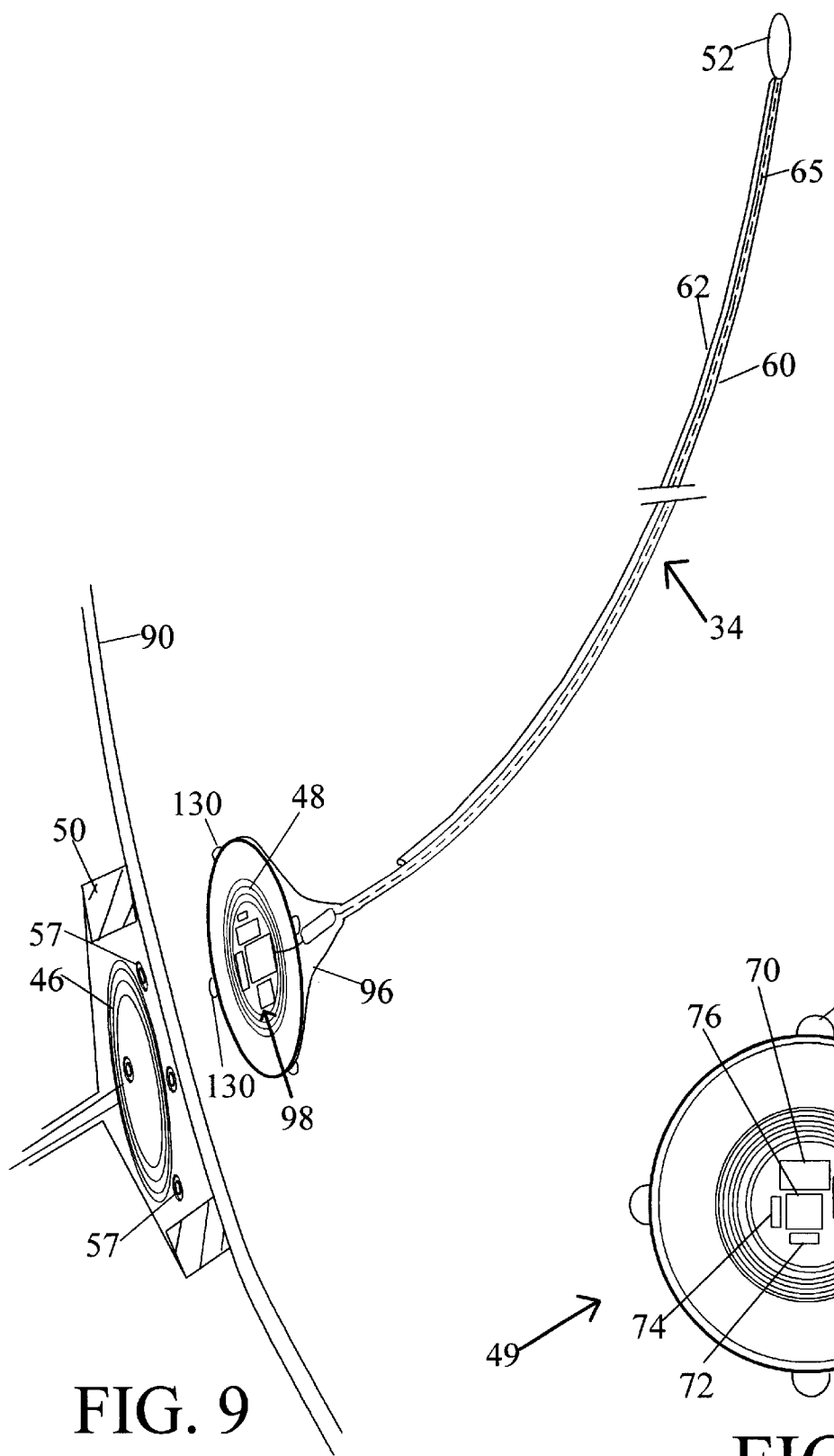
FIG. 9 is a diagram showing the implanted lead-receiver underneath the skin, also showing the relative position of the external coil
FIG. 10 is a diagram showing the proximal end of the lead-receiver.
Figure 11:
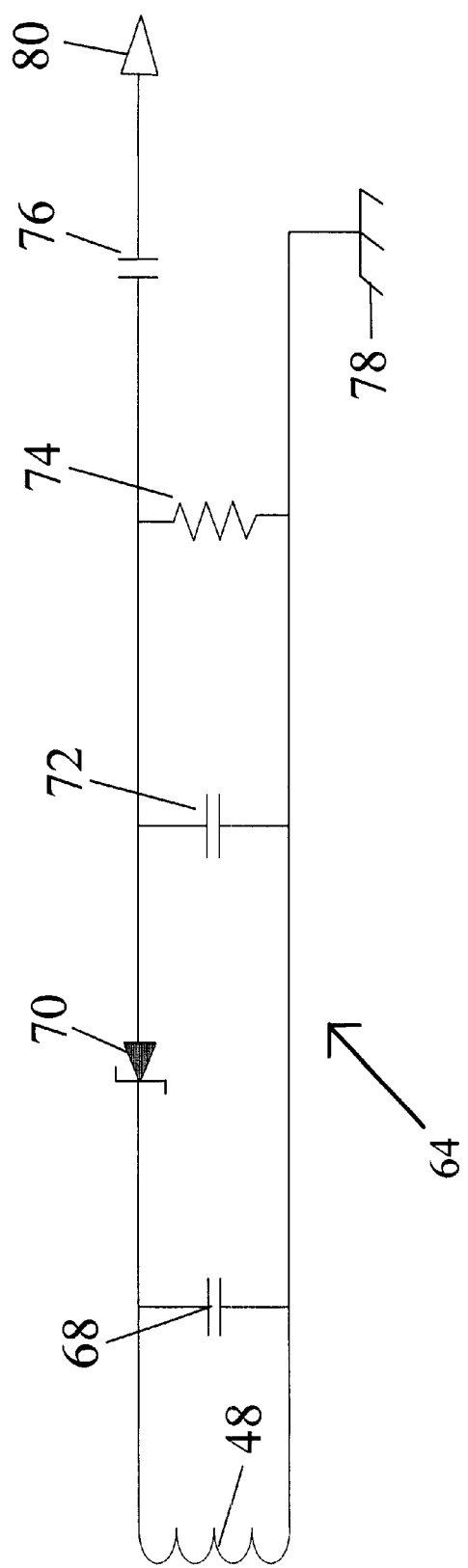
FIG. 11 is a diagram of circuitry within the proximal portion of the implanted lead- receiver.

Referring to FIG. 9, the implantable lead-receiver 34 looks somewhat like a golf "tee" and is the only implantable portion of the system. The "head" or proximal end 49 contains the coil 48 and electronic circuitry (hybrid) 98 which is hermetically sealed, and covered with silicone. It also has four anchoring sleeves 130 for tying it to subcutaneous tissue. FIG. 10 is a close-up view of the proximal portion 49 of the lead-receiver 34 containing the circuitry (hybrid) 98. This circuitry is shown schematically in FIG. 11. A coil 48 (preferably approximately 15 turns) is directly connected to the case 78. The external stimulator 42 and external patch 36 transmit the pulsed alternating magnetic field to receiver 64 where the stimulus pulses are detected by coil 48 and transmitted to the stimulus site, which is the vagus nerve 54. When exposed to the magnetic field of transmitter 36, coil 48 converts the changing magnetic field into corresponding voltages with alternating polarity between the coil ends. A capacitor 68 is used to tune coil 48 to the high-frequency of the transmitter 36.

The capacitor 68 increases the sensitivity and the selectivity of the receiver 64, which is made sensitive to frequencies near the resonant frequency of the tuned circuit and less sensitive to frequencies away from the resonant frequency. A zenor diode 70 in the current path is used for regulation and to allow the current that is produced by the alternating voltage of the coil to pass in one direction only. A capacitor 72 and resistor 74 filter-out the high-frequency component of the receiver signal and thereby leave a current of the same duration as the burst of the high-frequency signal. Capacitor 76 blocks any net direct current to the stimulating electrode tip 80, which is made of platinum/iridium (90%–10%). Alternatively, the stimulating electrode can be made of platinum or platinum/iridium in ratio's such as 80% Platinum and 20% Iridium.

The circuit components are soldered in a conventional manner to an upper conductive layer on a printed circuit board. The case 78 is connected to the coil 48 and is made of titanium. The case 78 also serves as the return electrode (anode). The surface area of the anode exposed to the tissue is much greater than the surface area of the stimulating electrode 80 (cathode). Therefore, the current density at the anode is too low to unduly stimulate tissue that is in contact with the anode. Alternatively, a bipolar mode of stimulation can also be used. In the bipolar mode of stimulation the cathode and anode are in close proximity to each other, and the far field effect is eliminated.

The body of the lead-receiver 34 is made of medical grade silicone (available from NuSil Technology, Applied silicone or Dow Chemical). Alternatively, the lead body 59 may be made of medical grade polyurethane (PU) of 55 D or higher durometer, such as available from Dow Chemical. Polyurethane is a stiffer material than silicone. Even though silicone is a softer material, which is favorable, it is also a weaker material than PU. Therefore, silicone coated with Teflon (PTFE) is preferred for this application. PTFE coating is available from Alpa Flex, Indianapolis, Ind.

Figure 12:
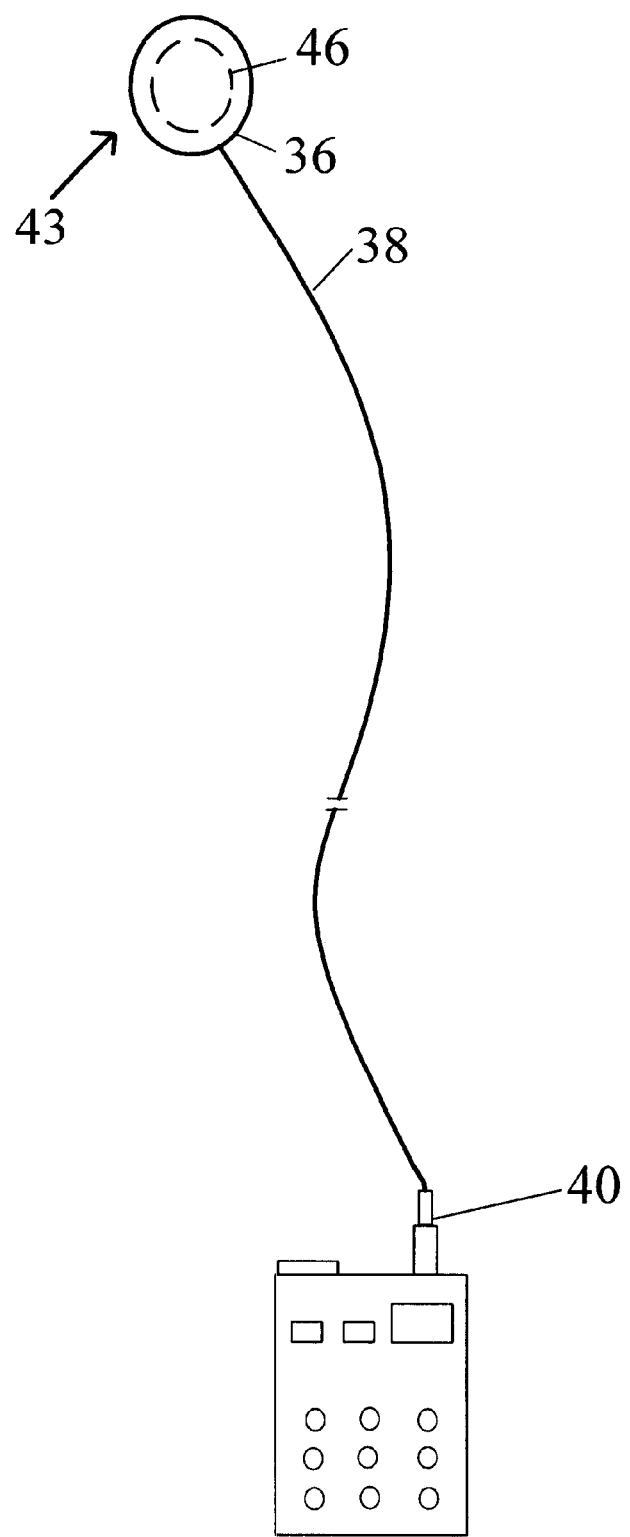
FIG. 12 is a diagram of an external patch and external pulse generator.

An external patch electrode 43 for inductive coupling is shown in FIG. 12. One end of the patch electrode contains the coil 46, and the other end is fitted to the external stimulator 42 via an adapter 40. The external patch electrode 43, is a modification of the patch electrode available from TruMed Technologies, Burnsville, Minn.

Figure 13:
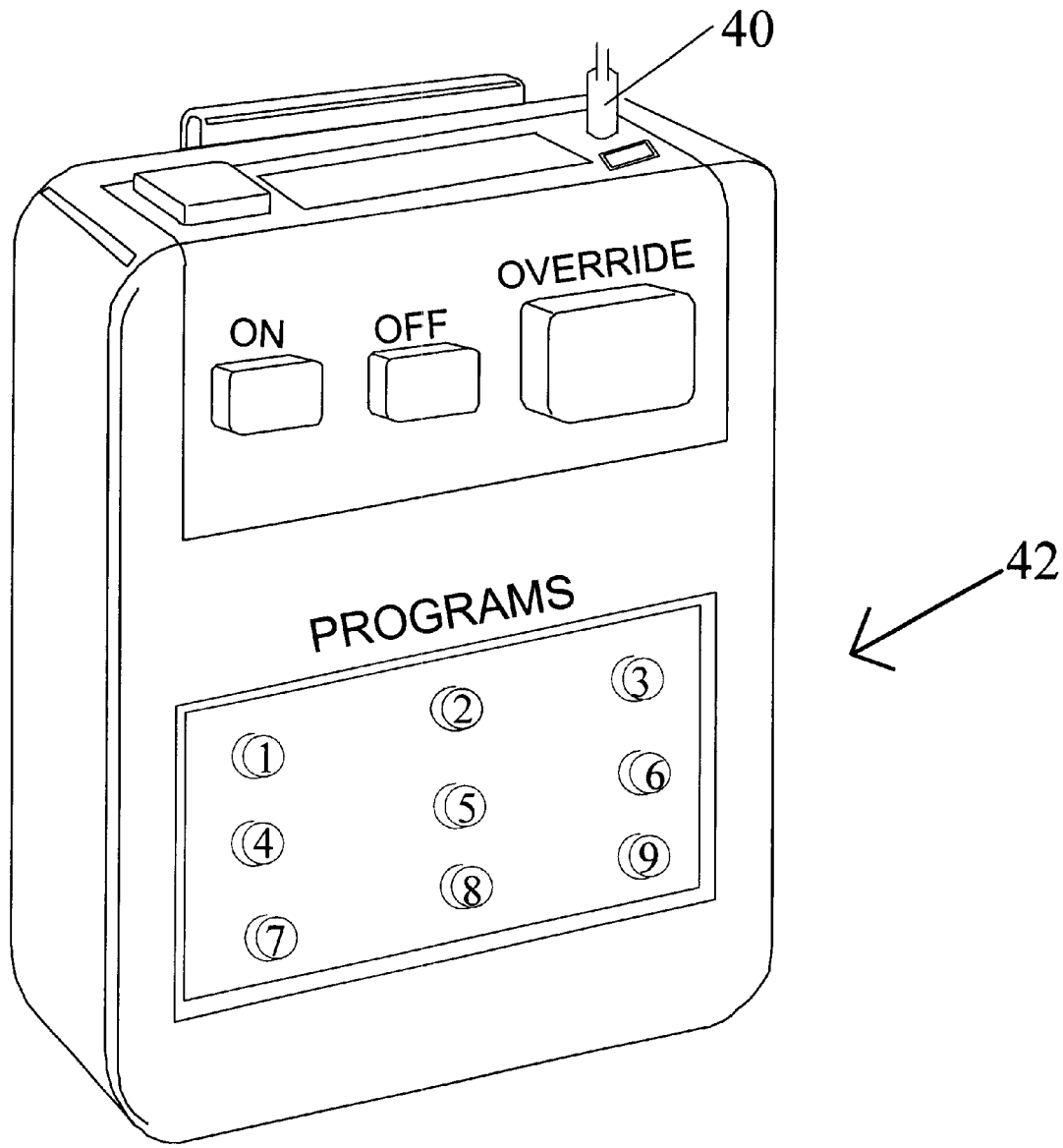
FIG. 13 Is a prospective view of an external pulse generator.

FIG. 13 shows a front view of an external stimulator 42, which is slightly larger than a conventional pager. The external stimulator 42 contains the circuitry and rechargeable or replaceable power source. The external stimulator 42 has two modes of operation. In the first mode of operation there are limited number of predetermined programs. The number of programs can be any reasonable number, say up to 60 programs. Such a number is considered within the scope of the invention. For patient convenience the presently preferred embodiment contains nine predetermined programs. These programs differ in stimulus intensity, pulse width, frequency of stimulation, and on-off timing sequence, e.g. "on" for 10 seconds and "off" for 50 seconds in repeating cycles. For patient safety, any number of these programs may be locked-out by the manufacturer or physician. In the second mode, the patient, or caretaker may activate the stimulation on at any time. This mode is useful, for example, in epileptic patients that have the characteristic "aura", which are sensory signs immediately preceding the convulsion that many epileptics have. When the device is turned on, a green light emitting diode (LED) indicates that the device is emitting electrical stimulation.

Pre-determined programs are arranged in such a way that the aggressiveness of the therapy increases from program #1 to Program #9. Thus the first three programs provide the least aggressive therapy, and the last three programs provide the most aggressive therapy.

The following are examples of least aggressive therapy.
Program #1:
    1.0 mA current output, 0.2 msec pulse width, 15 Hz frequency, 15 sec ON time-1.0 min OFF time, in repeating cycles.
Program #2:
    1.5 mA current output, 0.3 msec pulse width, 20 Hz frequency, 20 sec ON time-2.0 min OFF time, in repeating cycles.
The following are examples of intermediate level of therapy.
Program #5:
    2.0 mA current output, 0.2 msec pulse width, 25 Hz frequency, 20 sec ON time-1.0 min OFF time, in repeating cycles.
Program #6:
    2.0 mA current output, 0.25 msec pulse width, 25 Hz frequency, 30 sec ON time-1.0 min OFF time, in repeating cycles.
The following are examples of most aggressive therapy.
Program #8:
    2.5 mA current output, 0.3 msec pulse width, 30 Hz frequency, 40 sec ON time-1.5 min OFF time, in repeating cycles.
Program #9:
    3.0 mA current output, 0.4 msec pulse width, 30 Hz frequency, 30 sec ON time-1.0 min OFF time, in repeating cycles.

The majority of patients will fall into the category that require an intermediate level of therapy, such as program #5. The above are examples of the pre-determined programs that are delivered to the vagus nerve. The actual parameter settings for any given patient may deviate somewhat from the above.

Figure 14:
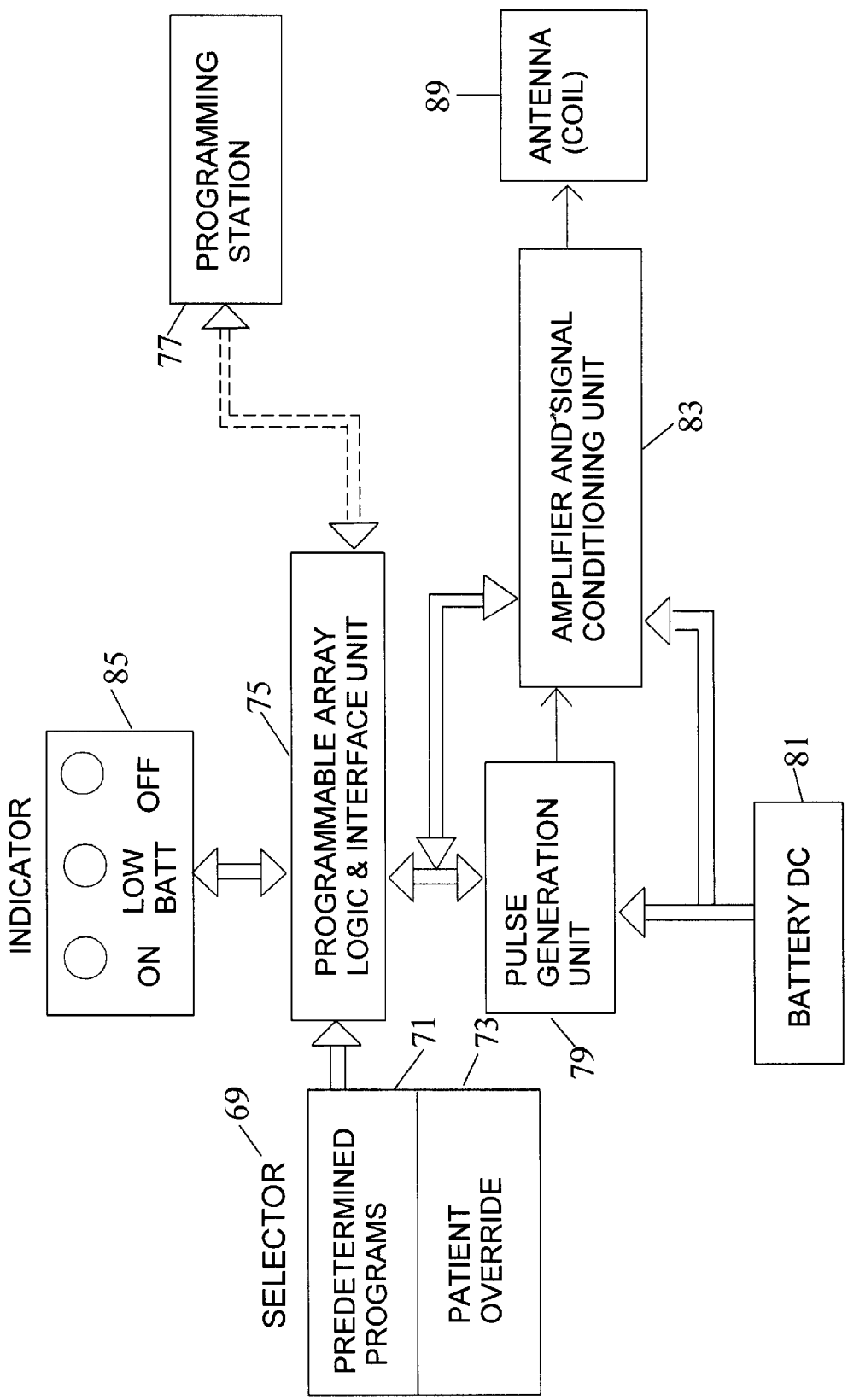
FIG. 14A is a top level block diagram of the external stimulator.
FIG. 14B is a block diagram of programmable array logic interfaced to the programming station.
FIG. 14C is a block diagram showing details of programmable logic array unit.
FIG. 14D diagram showing details of the interface between the programmable array logic and interface unit.
FIG. 14E is a diagram showing the circuitry of the pulse generator.
Figure 14:
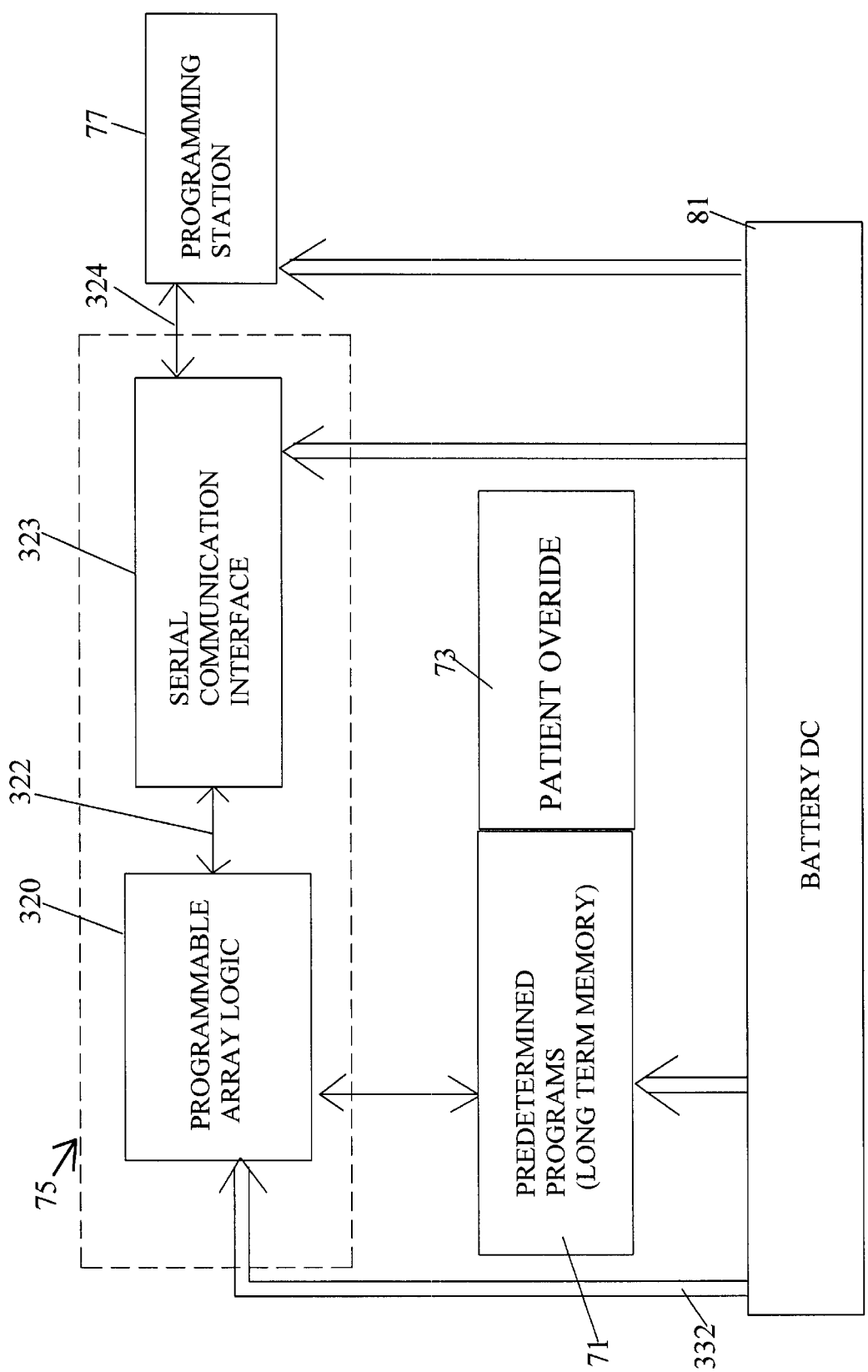
Figure 14:
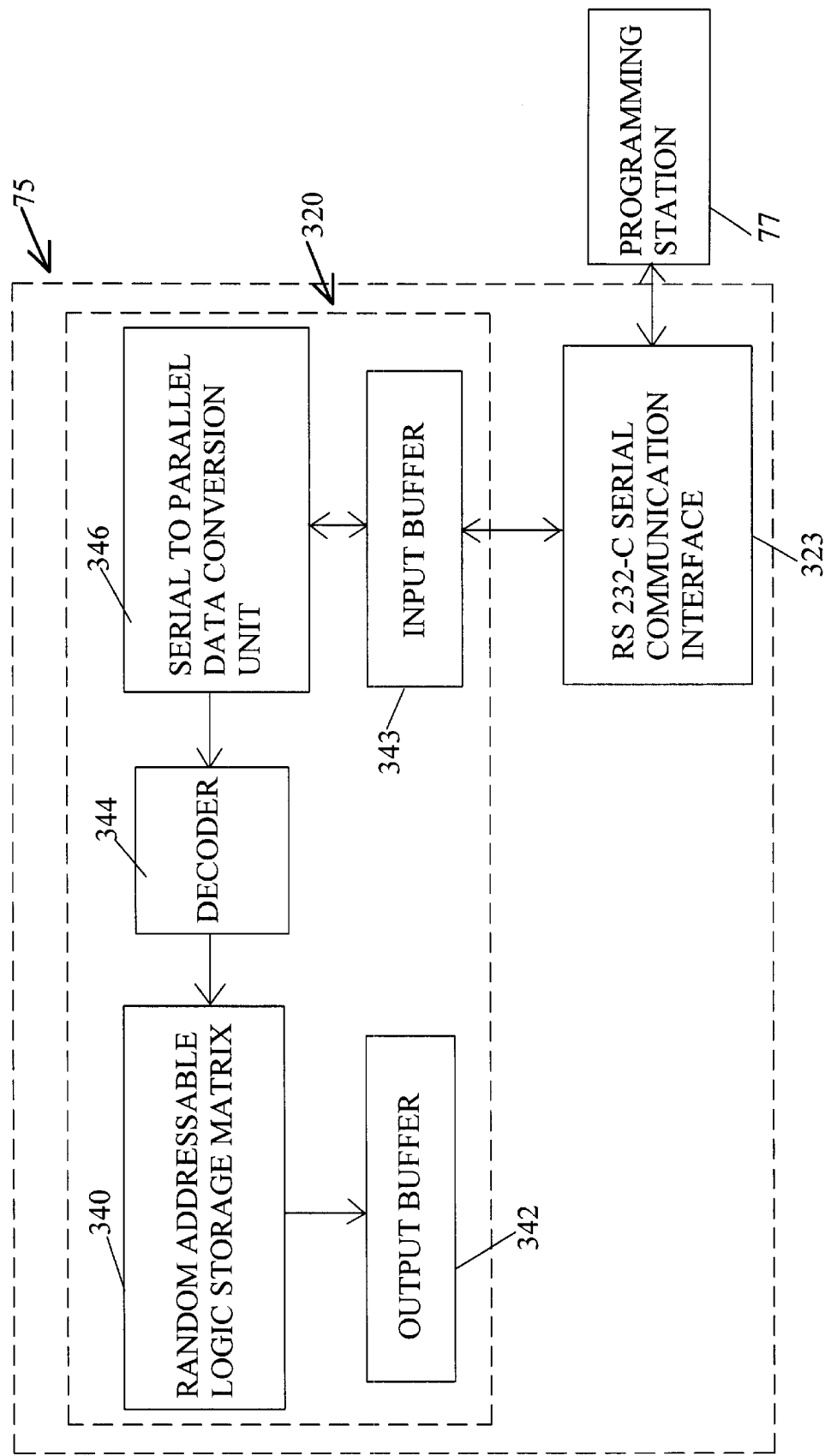
Figure 14:
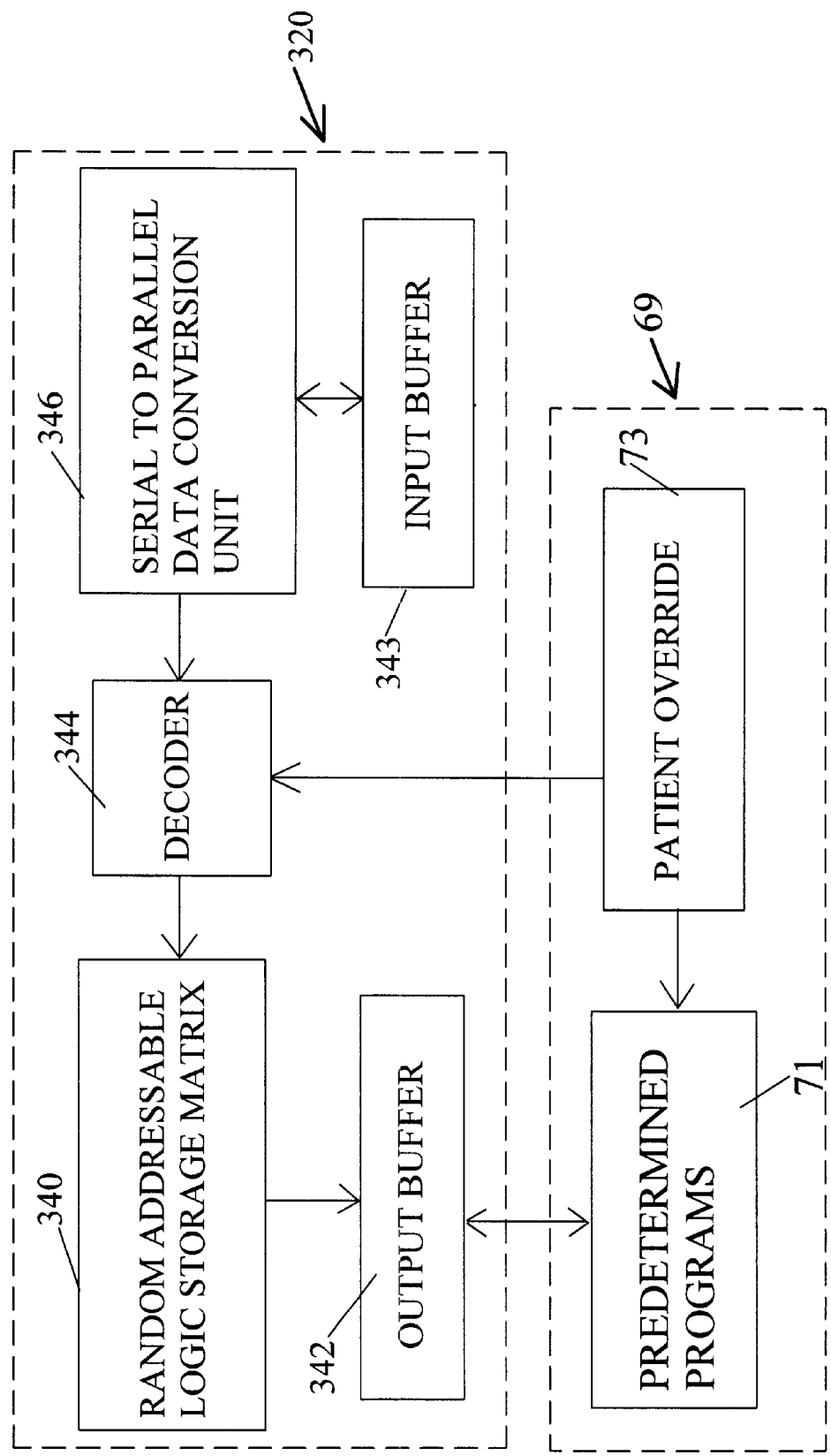

FIG. 14A shows a top level block diagram of the external stimulator 42. As previously mentioned, there are two modes of stimulation with the external stimulator 42. The first mode is a series of pre-determined standard programs 71, differing in the aggressiveness of the therapy. The second mode is patient override 73, where upon pressing a button, the device immediately goes into the active mode. The selector 69 which comprises of pre-determined programs 71 and patient override 73 feeds into programmable control logic 75. The programmable control logic 75 controls the pulse frequency oscillator 79. The output of the pulse frequency oscillator 79 is amplified 83, filtered and provided to the external coil (antenna) 89, which is then transmitted to the implanted receiver 34 for stimulation of the nerve. The programmable control logic 75 is connected to an indicator 85 showing on-off status, as well as the battery status. The external stimulator 42 is powered by a DC battery 81. A programming station 77 provides the capability to download and change programs if the need arises.

FIG. 14B shows the Programmable Array Logic and Interface Unit 75 interfaced to the Programming Station 77. The programming station allows the user to change and program the parameters for various stimulation programs. The programming station is connected to the Programmable Array Unit 75 with an RS232-C serial connection 324. The main purpose of the serial line interface is to provide an RS232-C standard interface. This method enables any portable computer with a serial interface to communicate and program the parameters for storing the various programs. The serial communication interface receives the serial data, buffers this data and converts it to a 16 bit parallel data 323. The Programmable Array Logic 320 component of Programmable Array Unit 75 receives the parallel data bus and stores or modifies the data into a random access matrix 320. This array of data also contains special logic and instructions along with the actual data. These special instructions also provide an algorithm for storing, updating and retrieving the parameters from long-term memory. The Programmable Array Unit 320, interfaces with Long Term Memory to store the pre-determined programs 71. All the previously modified programs can be stored here for access at any time. The programs will consist of specific parameters and each unique program will be stored sequentially in long-term memory. A battery unit 81 is present to provide power to all the components shown above. The logic for the storage and decoding is stored in the Random Addressable Storage Matrix (RASM) 340.

FIG. 14C shows greater details for the Programmable Logic Array Unit 320. The Input Buffer block 343 is where the serial data is stored in temporary register storage. This accumulation allows for the serial to parallel conversion to occur. The serial to 16 bit parallel block sets up 16 bits of data 346, as created from the RS232-C serial data. This parallel data bus will communicate the data and the address information. The decoder block 344 decodes address information for the Random Addressable Logic Storage Matrix 340 from which to access the data i.e. programmer parameters. The Output Buffer 342 provides an interface to the Long Term Memory 71.

FIG. 14D shows schematically the details of the interface between the Programmable Array Logic 320 and Interface Unit 75 which is connected to the Predetermined Programs block (Long Term Memory) 71. The patient override 73 is essentially a control scheme for initializing or starting a program at any intermediate point. The Field Programmable array provides a reconfigurable mechanism to store data and associated instructions for the programs. It supports adding modifying or retrieving the data from a Random Addressable Logic Storage Matrix 340. This is also a widely accepted scheme for treating "flexible" logic description and control. It is flexible by providing the ability to reprogram and even redesign existing programs previously installed as predetermined programs. The block diagram shown in FIG. 14A allows the health care provider to select stimulation programs of choice. This allows the authorized user to create, modify and select for execution, programs to use for a particular time period.

Figure 14E:
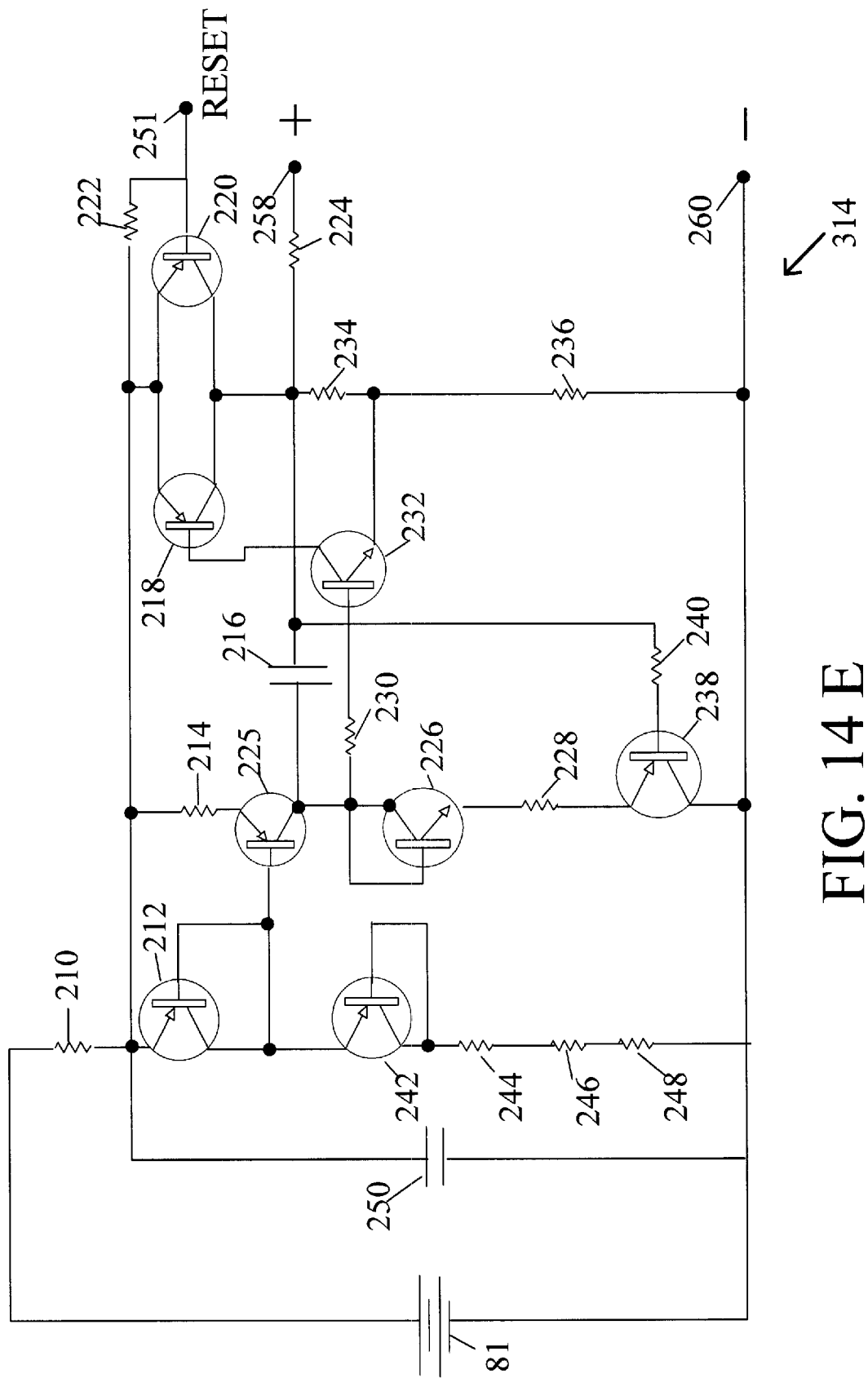

The pulse generator circuitry, shown schematically in FIG. 14E, exhibits typical multivibrator functionality. This circuit produces regularly occurring pulses where the amplitude, pulse width and frequency is adjustable. The battery 81 is the main external power source for this circuit. The capacitor 250 is connected in parallel with the battery 252. The combination of transistors 212, 242 and 225, and resistors 210, 244, 246 and 248 acts as a constant current source generated at the collector of transistor 226. The transistor 212 has collector connected to the emitter of transistor 242 and base of transistor 225. The transistors 212 and 242 are connected to provide a constant voltage drop. Likewise, transistor 226 also acts as a diode with a resistor 228 connected in series and further connected to the negative terminal of the line at terminal 260. Capacitor 216 provides timing characteristics and its value helps determine pulse width and pulse frequency. The output of the oscillator appears at terminal 258.

Initially, the capacitor 216 gets charged with current from the path of resistor 234 and 236 while all the transistors are turned off. As the capacitor charges up transistor 232 will become forward biased and current will flow via resistors 230 and 236 from the base to emitter resistors. This action turns on the transistor 218 and the positive voltage from the power supply 81 is made available at the base of transistor 238 through resistor 240. This results in the transistor 238 getting turned on. The conduction of transistor 238 causes capacitor 216 to discharge. The time constant for the charge and discharge of capacitor 216 is determined by value of the resistors 228 and 240 and capacitor 216. After the time constant, transistor 232 turns off, and this in turn turns off transistors 238 and 218. A reset mechanism for this multivibrator can be provided by setting a positive voltage, for example 2.5 volts, to the base of transistor 220. This positive increase in voltage turns on transistor 220 followed by transistor 238. The turning on of transistor 238 discharges the capacitor 216 and the reset operation is complete.

Conventional integrated circuits are used for the logic, control and timing circuits. Conventional bipolar transistors are used in radio-frequency oscillator, pulse amplitude ramp control and power amplifier. A standard voltage regulator is used in low-voltage detector. The hardware and software to deliver these pre-determined programs is well known to those skilled in the art.

The fabrication of the lead-receiver 34 is designed to be modular. Thus, several different components can be mixed and matched without altering the functionality of the device significantly. As shown in FIG. 9, the lead-receiver 34 components are the proximal end 49 (containing coil 48, electrical circuitry 98, and case 78), the lead body 59 containing the conductor 65, and the distal electrode (cathode) 52. In the modular design concept, several design variables are possible, as shown in the table below.

Table of lead-receiver design variables

| Proximal End | | | | | | Distal End |
|---|---|---|---|---|---|---|
| Circuitry and Return electrode | Lead body- Lumens | Lead body- Insulation materials | Lead- Coating | Conductor (connecting proximal and distal ends) | Electrode- Material | Electrode- Type |
| Bipolar | Single | Polyurethane | Lubricious (PVP) | Alloy of Nickel-Cobalt | Pure Platinum | Standard ball electrode |
| Unipolar | Double | Silicone | Antimicrobial | | Platinum-Iridium (Pt/Ir) alloy | Hydrogel electrode |
| | Triple | Silicone with Polytetrafluoroethylene (PTFE) | Anti-inflammatory | | Pt/Ir coated with Titanium Nitride | Spiral electrode |
| | Coaxial | | | | Carbon | Steroid eluting Fiber electrode |

Either silicone or polyurethane is suitable material for this implantable lead body 59. Both materials have proven to have desirable qualities which are not available in the other. Permanently implantable pacemaker leads made of polyurethane are susceptible to some forms of degradation over time. The identified mechanisms are Environmental Stress Cracking (ESC) and Metal Ion Oxidation (MIO). For this reason silicone material is slightly preferred over polyurethane.

Nerve-electrode interaction is an integral part of the stimulation system. As a practical benefit of modular design, any type of electrode described below can be used as the distal (cathode) stimulating electrode, without changing fabrication methodology or procedure significantly. When a standard ball electrode made of platinum or platinum/iridium is placed next to the nerve, and secured in place, it promotes an inflammatory response that leads to a thin fibrotic sheath around the electrode over a period of 1 to 6 weeks. This in turn leads to a stable position of electrode relative to the nerve, and a stable electrode-tissue interface, resulting in reliable stimulation of the nerve chronically without damaging the nerve.

Figure 15:
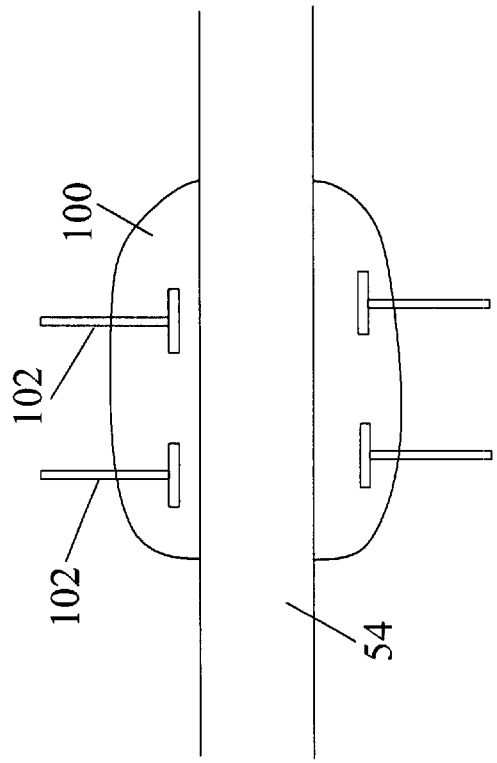
FIG. 15 is a diagram of a hydrogel electrode.

Alternatively, other electrode forms that are non-traumatic to the nerve such as hydrogel, platinum fiber, or steroid elution electrodes may be used with this system. The concept of hydrogel electrode for nerve stimulation is shown schematically in FIG. 15. The hydrogel material 100 is wrapped around the nerve 54, with tiny platinum electrodes 102 being pulled back from nerve. Over a period of time in the body, the hydrogel material 100 will undergo degradation and there will be fibrotic tissue buildup. Because of the softness of the hydrogel material 100, these electrodes are non-traumatic to the nerve.

Figure 16:
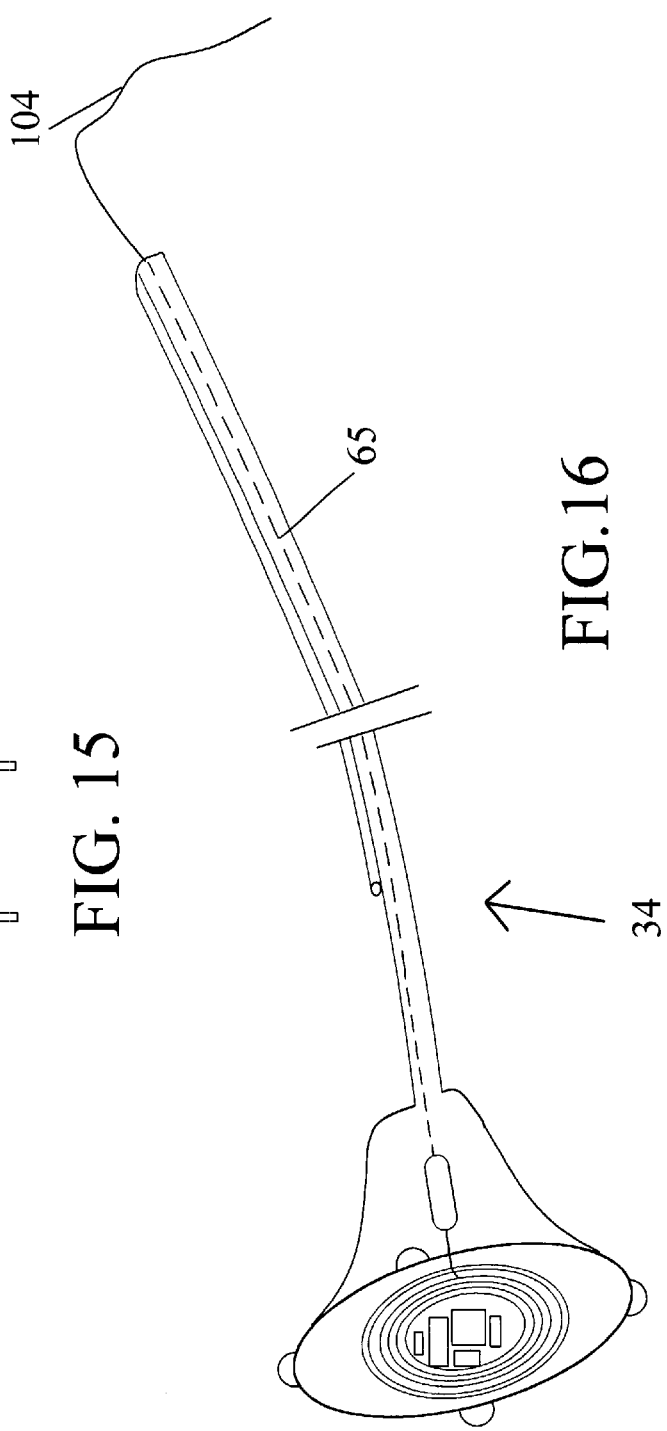
FIG. 16 is a diagram of a lead-receiver utilizing a fiber electrode at the distal end.
Figure 17:
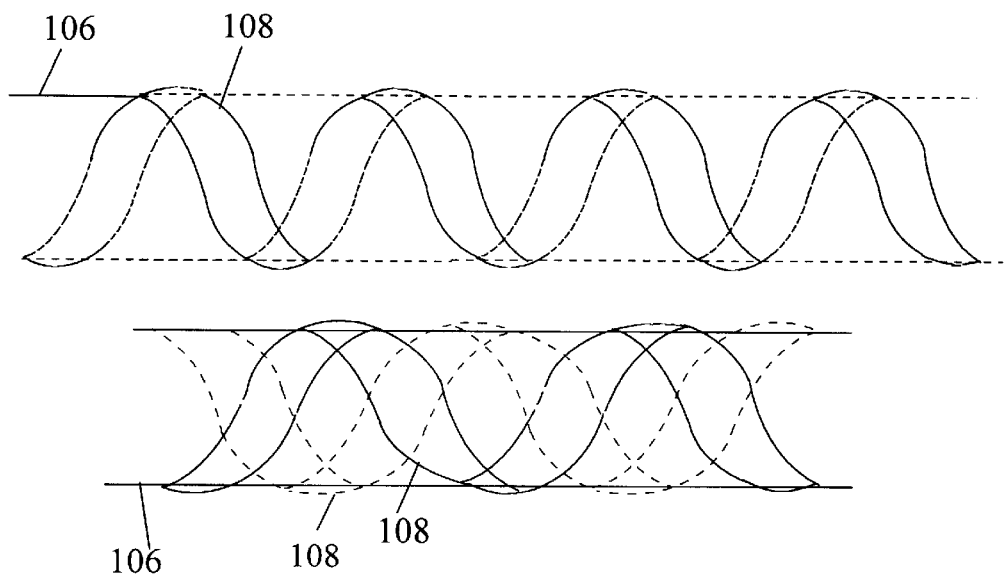
FIG. 17 is a diagram of a fiber electrode wrapped around Dacron polyester.
Figure 18:
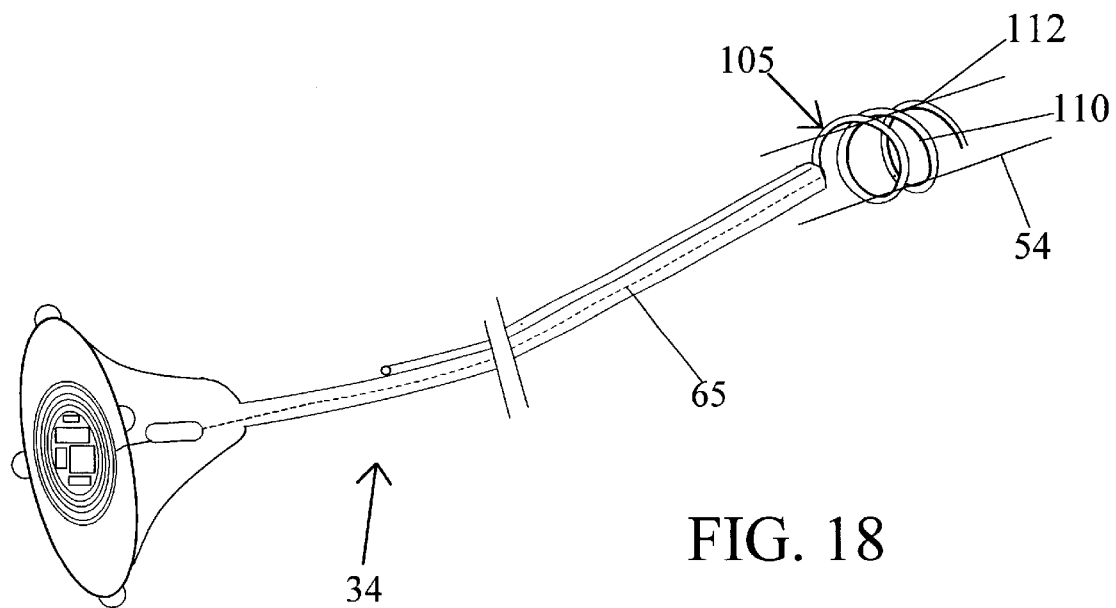
FIG. 18 is a diagram of a lead-receiver with a spiral electrode.

The concept of platinum fiber electrodes is shown schematically in FIG. 16. The distal fiber electrode 104 attached to the lead-receiver 34 may be platinum fiber or cable, or the electrode may be thin platinum fiber wrapped around Dacron polyester or Polyimide 106. As shown in FIG. 17, the platinum fibers 108 may be woven around Dacron polyester fiber 106 or platinum fibers 108 may be braided. At implant, the fiber electrode 104 is loosely wrapped around the surgically isolated nerve, then tied loosely so as not to constrict the nerve or put pressure on the nerve. As a further extension, the fiber electrode may be incorporated into a spiral electrode 105 as is shown schematically in FIG. 18. The fiber electrode 110 is on the inner side of polyurethane or silicone insulation 112 which is heat treated to retain its spiral shape.

Figure 19:
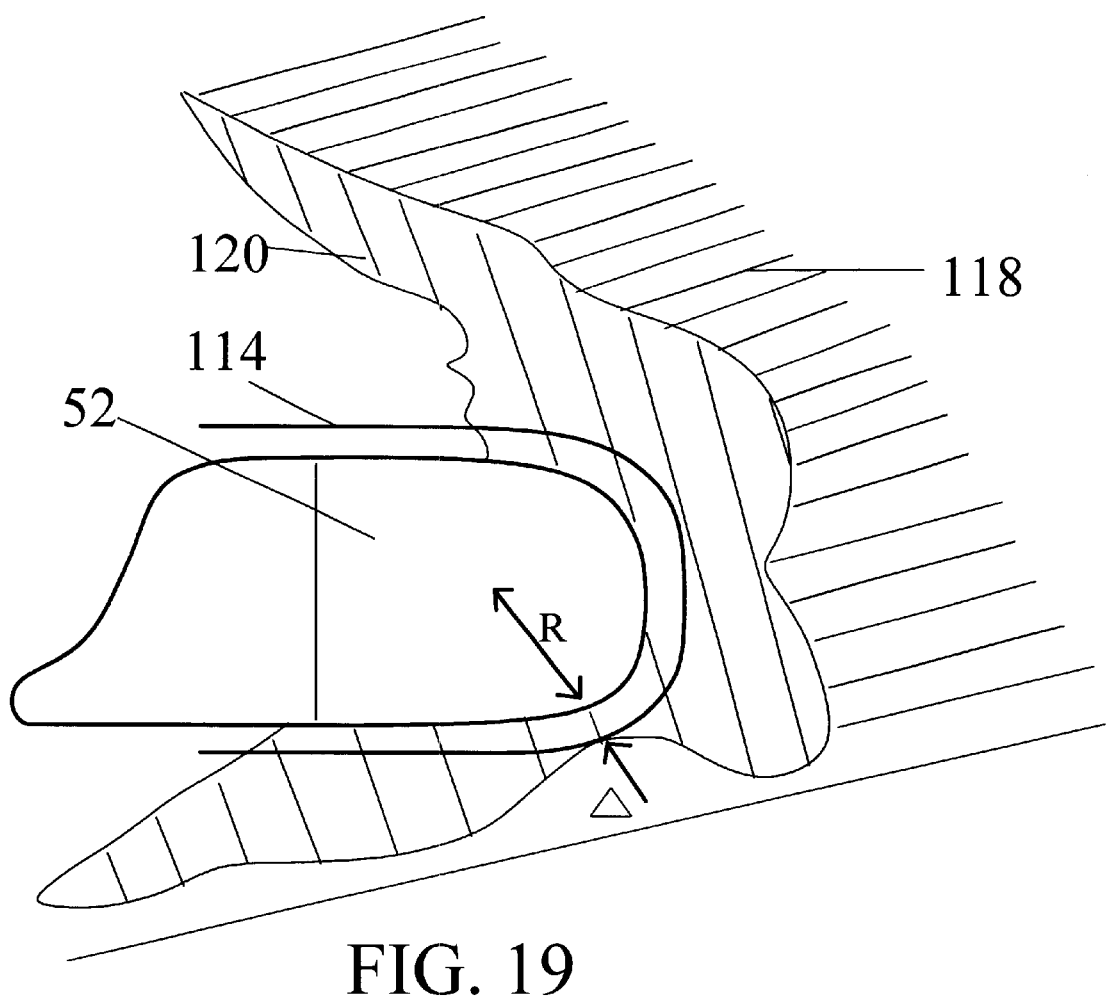
FIG. 19 is a diagram of an electrode embedded in tissue.

Alternatively, steroid elution electrodes may be used. After implantation of a lead in the body, during the first few weeks there is buildup of fibrotic tissue in-rowth over the electrode and to some extent around the lead body. This fibrosis is the end result of body's inflammatory response process which begins soon after the device is implanted. The fibrotic tissue sheath has the net effect of increasing the distance between the stimulation electrode (cathode) and the excitable tissue, which is the vagal nerve in this case. This is shown schematically in FIG. 19, where electrode 52 when covered with fibrotic tissue becomes the "virtual" electrode 114. Non-excitable tissue is depicted as 120 and excitable tissue as 118. A small amount of corticosteroid, dexamethasone sodium phosphate commonly referred to as "steroid" or "dexamethasone" placed inside or around the electrode, has significant beneficial effect on the current or energy threshold, i.e. the amount of energy required to stimulate the excitable tissue. This is well known to those familiar in the art, as there is a long history of steroid elution leads in cardiac pading application. It takes only about 1 mg of dexamethasone to produce the desirable effects. Three separate ways of delivering the steroid drug to the electrode nerve-tissue interface are being disclosed here. Dexamethasone can be placed inside an electrode with microholes, it can be placed adjacent to the electrode in a silicone collar, or it can be coated on the electrode itself.

Figure 20:
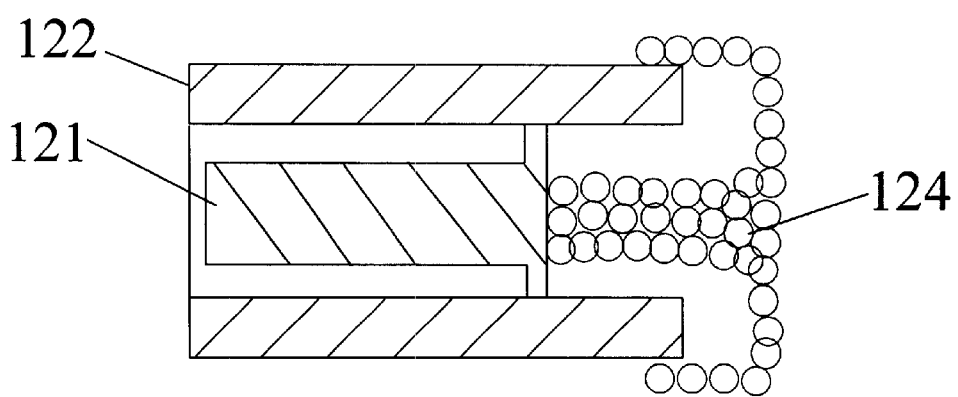
FIG. 20 is a diagram of an electrode containing steroid drug inside.

Dexamethasone inside the stimulating electrode is shown schematically in FIG. 20. A silicone core that is impregnated with a small quantity of dexamethasone 121, is incorporated inside the electrode. The electrode tip is depicted as 124 and electrode body as 122. Once the lead is implanted in the body, the steroid 121 elutes out through the small holes in the electrode. The steroid drug then has anti-inflammatory action at the electrode tissue interface, which leads to a much thinner fibrotic tissue capsule.

Another way of having a steroid eluting nerve stimulating electrode, is to have the steroid agent placed outside the distal electrode 52 in a silicone collar 126. This is shown schematically in FIG. 21. Approximately 1 mg of dexamethasone is contained in a silicone collar 126, at the base of the distal electrode 52. With such a method, the steroid drug elutes around the electrode 52 in a similar fashion and with similar pharmacokinetic properties, as with the steroid drug being inside the electrode.

Another method of steroid elution for nerve stimulation electrodes is by coating of steroid on the outside (exposed) surface area of the electrode. This is shown schematically in FIG. 22. Nafion is used as the coating matrix. Steroid membrane coating on the outside of the electrode is depicted as 128. The advantages of this method are that it can easily be applied to any electrode, fast and easy manufacturing, and it is cost effective. With this method, the rate of steroid delivery can be controlled by the level of sulfonation.

A schematic representation of the cross section of different possible lumens is shown in FIG. 23. The lead body 59 can have one, two, or three lumens for conducting cable, with or without a hollow lumen. In the cross sections, 132A–F represents lumens(s) for conducting cable, and 134A–C represents hollow lumen for aid in implanting the lead.

Additionally, different classes of coating may be applied to the implantable lead- receiver 34 after fabrication. These coatings fall into three categories, lubricious coating, anti-microbial coating, and anti-inflammatory coating.

The advantage of modular fabrication is that with one technology platform, several derivative products or models can be manufactured. As a specific practical example, using a silicone lead body platform, three separate derivative or lead models can be manufactured by using three different electrodes such as standard electrode, steroid electrode or spiral electrode. This is made possible by designing the fabrication steps such that the distal electrodes are assembled at the end, and as long as the electrodes are mated to the insulation and conducting cable, the shape or type of electrode does not matter. Similarly, different models can be produced by taking a finished lead and then coating it with lubricious coating or antimicrobial coating. In fact, considering the design variables disclosed in table 1, a large number of combinations are possible. Of these large number of possible combinations, about 6 or 7 models are planned for manufacturing. These include lead body composed of silicone and PTFE with standard ball electrodes made of platinum/iridium alloy, and silicone lead body with spiral electrode.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. An external pulse generator for neuromodulation treatment of at least one of neurologic, neuropsychiatric, and urological disorders comprising:
   a) a power source, primary coil, and circuitry to provide electrical signals; and
   b) at least two pre-determined programs to control the electrical signals generated by said pulse generator whereby neuromodulation treatment is provided.

2. The pulse generator of claim 1, wherein said pulse generator is adapted to be used with an implanted receiving means for neuromodulation.

3. The pulse generator of claim 1, wherein said neuromodulation treatment includes one of depression, migraine, partial complex epilepsy, generalized epilepsy, involuntary movement disorders, dementia including Alzheimer's disease, neurogenic/psychogenic pain, obsessive compulsive disorders, urinary incontinence, bladder control and the like.

4. The pulse generator of claim 1, wherein said pre-determined programs are capable of being modified to modify said electrical signal.

5. The pulse generator of claim 1, further comprising a program selection mechanism wherein at least two pre-determined may be selectively operated.

6. The pulse generator of claim 1, wherein said at least one pre-determined program may be locked out for patient activation.

7. The pulse generator of claim 1, wherein said at least one pre-determined programs may not be locked out for patient activation.

8. The pulse generator of claim 1, wherein said emitted electrical signals are capable of inductively coupling to an implanted lead-receiver.

9. The pulse generator of claim 1, wherein said pre-determined programs consist of unique combination of parameters comprising of pulse amplitude, pulse width, frequency of nerve stimulation, and on-off time.

10. The pulse generator of claim 9, wherein said pulse amplitude can range from 0.2 milliamps to 6 milliamps.

11. The pulse generator of claim 9, wherein said pulse width can range from 0.1 milliseconds to 4.0 milliseconds.

12. The pulse generator of claim 9, wherein said nerve stimulation frequency can range from 10 Hz to 200 Hz.

13. The pulse generator of claim 9, wherein said on time can range from 30 seconds to 4 hour.

14. The pulse generator of claim 9, wherein said off time can range from 1 minute to 8 hours.

15. An external stimulator for electrical stimulation therapy for at least one of neurological, neuropsychiatric, and urological disorders comprising:
   a) a power source, primary coil, and circuitry to provide electrical signals and;
   b) at least two pre-determined programs to control the electrical signals generated by said external stimulator whereby electrical stimulation treatment is provided.

16. The pulse generator of claim 15, wherein said external stimulator is adapted to be used with an implanted receiving means for electrical stimulation therapy.

17. The external stimulator of claim 15, wherein said at least two predetermined programs may be manually disengaged.

18. The external stimulator of claim 15, wherein said stimulator is adapted to be used with an implanted receiving means for electrical stimulation therapy.

19. The external stimulator of claim 15, wherein said electrical stimulation therapy comprises for at least one of depression, migraine, partial complex epilepsy, generalized epilepsy, involuntary movement disorders, dementia including Alzheimer's disease, neurogenic/psychogenic pain, obsessive compulsive disorders, urinary incontinence, bladder control and the like.

20. The external stimulator of claim 15, wherein said pre-determined programs are capable of being modified to modify said electrical signal.

21. The external stimulator of claim 15, further comprising a program selection mechanism wherein at least two pre-determined may be selectively operated.

22. The external stimulator of claim 15, wherein said at least one pre-determined program may be locked out for patient activation.

23. The external stimulator of claim 15, wherein said at least one pre-determined programs may not be locked out for patient activation.

24. The external stimulator of claim 15, wherein said emitted electrical signals are capable of inductively coupling to an implanted lead-receiver.

25. The external stimulator of claim 15, wherein said pre-determined programs consist of unique combination of parameters comprising of pulse amplitude, pulse width, frequency of nerve stimulation, and on-off time.

26. The external stimulator of claim 25, wherein said pulse amplitude can range from 0.2 milliamps to 10 milliamps.

27. The external stimulator of claim 25, wherein said pulse width can range from 0.1 milliseconds to 4.0 milliseconds.

28. The external stimulator of claim 25, wherein said nerve stimulation frequency can range from 10 Hz to 100 Hz.

29. The external stimulator of claim 25, wherein said on-time can range from 30 seconds to 4 hours.

30. The external stimulator of claim 25, wherein said off-time can range from 1 minute to 8 hours.

31. An external stimulator for pulsed electrical therapy for at least one of neurological, neuropsychiatric, and urological disorders comprising:
   a) a power source, primary coil, and circuitry to provide electrical signals and;
   b) at least two pre-determined programs to control the electrical signals generated by said external stimulator whereby pulsed electrical therapy is provided.

32. The external stimulator of claim 31, wherein said external stimulator is adapted to be used with an implanted receiving means for pulsed electrical therapy.

33. The external stimulator of claim 31, wherein said at least two predetermined programs may be manually disengaged.

34. The external stimulator of claim 31, wherein said pulsed electrical therapy comprises for at least one of depression, migraine, partial complex epilepsy, generalized epilepsy, involuntary movement disorders, dementia including Alzheimer's disease, neurogenic/psychogenic pain, obsessive compulsive disorders, urinary incontinence bladder, control and the like.

35. The external stimulator of claim 31, wherein said pre-determined programs are capable of being modified to modify said electrical signal.

36. The external stimulator of claim 31, further comprising a program selection mechanism wherein at least two pre-determined may be selectively operated.

37. The external stimulator of claim 31, wherein said at least one pre-determined program may be locked out for patient activation.

38. The external stimulator of claim 31, wherein said at least one pre-determined programs may not be locked out for patient control.

39. The external stimulator of claim 31, wherein said emitted electrical signals are capable of inductively coupling to an implanted lead-receiver.

40. The external stimulator of claim 31, wherein said pre-determined programs consist of unique combination of parameters comprising of pulse amplitude, pulse width, frequency of nerve stimulation, and on-off time.

41. The external stimulator of claim 40, wherein said pulse amplitude can range from 0.2 milliamps to 10.0 milliamps.

42. The external stimulator of claim 40, wherein said pulse width can range from 0.1 milliseconds to 4.0 milliseconds.

43. The external stimulator external stimulator of claim 40, wherein said nerve stimulation frequency can range from 10 Hz to 200 Hz.

44. The external stimulator external stimulator of claim 40, wherein said on-time can range from 1 minute to 4 hour.

45. The external stimulator external stimulator of claim 40, wherein said off-time can range from 1 minute to 8 hours.

* * * * *